(12) United States Patent
Cheung et al.

(10) Patent No.: US 6,417,136 B2
(45) Date of Patent: *Jul. 9, 2002

(54) HYDROCARBON HYDROGENATION CATALYST AND PROCESS

(75) Inventors: Tin-Tack Peter Cheung; Darin B. Tiedtke; Marvin M. Johnson; Gary A. Delzer, all of Bartlesville, OK (US)

(73) Assignee: Phillips Petroleum Company, Bartlesville, OK (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/398,664

(22) Filed: Sep. 17, 1999

(51) Int. Cl.⁷ .................................. B01J 23/58
(52) U.S. Cl. .................. 502/330; 502/333; 502/341; 502/346; 502/348
(58) Field of Search .................. 502/325, 326, 502/327, 333, 330, 347, 341, 346, 348, 329, 331

(56) References Cited

U.S. PATENT DOCUMENTS

| | | | | |
|---|---|---|---|---|
| 3,668,151 A | * | 6/1972 | Walker ........................ | 252/466 |
| 3,880,776 A | | 4/1975 | Box, Jr. et al. ............. | 252/466 |
| 3,923,690 A | * | 12/1975 | Vogt et al. ................. | 252/447 |
| 4,201,760 A | * | 5/1980 | Arendt et al. ............... | 423/600 |
| 4,484,015 A | | 11/1984 | Johnson et al. ............. | 585/262 |
| 4,565,803 A | | 1/1986 | Schoenthal et al. .......... | 502/303 |
| 4,898,845 A | * | 2/1990 | Datta et al. ................... | 502/3 |
| 5,057,206 A | * | 10/1991 | Engel et al. .................. | 208/143 |
| 5,095,166 A | * | 3/1992 | Forschner et al. ........... | 585/653 |
| 5,219,816 A | * | 6/1993 | Zhou et al. .................. | 505/223 |
| 5,407,459 A | * | 4/1995 | Breault et al. ................ | 75/303 |
| 5,475,173 A | | 12/1995 | Cheung et al. .............. | 585/259 |
| 5,482,615 A | | 1/1996 | Meitzner et al. ............. | 208/139 |
| 5,489,565 A | | 2/1996 | Cheung et al. .............. | 502/325 |
| 5,536,695 A | * | 7/1996 | Blejean et al. .............. | 502/327 |
| 5,688,984 A | | 11/1997 | Ohdan et al. ................ | 558/277 |
| 5,753,583 A | | 5/1998 | Heineke et al. .............. | 585/326 |
| 5,866,735 A | | 2/1999 | Cheung et al. .............. | 585/273 |

* cited by examiner

Primary Examiner—Bekir L. Yildirim
(74) Attorney, Agent, or Firm—Charles W. Stewart

(57) ABSTRACT

A catalyst composition is provided which can be used for hydrogenating a highly unsaturated hydrocarbon such as an alkyne or a diolefin. The catalyst composition contains palladium, a catalyst component of either silver or an alkali metal compound, or both silver and an alkali metal compound, and a metal aluminate catalyst support. Such metal aluminate catalyst support is prepared by a process of incorporating alumina with a metal component, preferably impregnating alumina with a melted metal component, to thereby provide a metal-incorporated alumina followed by drying and high temperature calcining to thereby provide a metal aluminate catalyst support. The catalyst composition disclosed can be used for hydrogenating a highly unsaturated hydrocarbon to a less unsaturated hydrocarbon. The process involves contacting a highly unsaturated hydrocarbon with a catalyst composition in the presence of hydrogen under a hydrogenation condition sufficient to effect a hydrogenation of the highly unsaturated hydrocarbon.

108 Claims, No Drawings

HYDROCARBON HYDROGENATION CATALYST AND PROCESS

BACKGROUND OF THE INVENTION

This invention relates to a supported metal catalyst composition, a process of making such supported metal catalyst composition, and to a process of using such supported metal catalyst composition for hydrogenating a highly unsaturated hydrocarbon.

It is known to one skilled in the art that a less unsaturated hydrocarbon compound can be produced by a thermal cracking process. For example, a fluid stream containing a saturated hydrocarbon such as, for example, ethane, propane, butane, pentane, naphtha, and the like and combinations thereof can be fed into a thermal (or pyrolytic) cracking furnace. Within the furnace, the saturated hydrocarbon is converted to a less unsaturated hydrocarbon compound such as, for example, ethylene or propylene. Such less unsaturated hydrocarbons are an important class of chemicals that find a variety of industrial uses. For example, ethylene can be used as a monomer or comonomer for producing a polyolefin. Other uses of unsaturated hydrocarbons are well known to one skilled in the art.

However, such less unsaturated hydrocarbon produced by a thermal cracking process generally contains an appreciable amount of less desirable highly unsaturated hydrocarbon(s) such as alkyne(s) or diolefin(s). For example, ethylene produced by thermal cracking of ethane is generally contaminated with a highly unsaturated hydrocarbon, such as acetylene, which must be selectively hydrogenated to a less unsaturated hydrocarbon, such as ethylene, but not to a saturated hydrocarbon such as ethane, in a hydrogenation reaction.

In addition, catalysts comprising palladium and an inorganic support, such as alumina, are known catalysts for the hydrogenation of highly unsaturated hydrocarbons such as alkynes and/or diolefins. In the case of the selective hydrogenation of acetylene to ethylene, a palladium and silver catalyst supported on alumina can be employed. See for example U.S. Pat. Nos. 4,404,124 and 4,484,015, the disclosures of which are incorporated herein by reference. The operating temperature for this hydrogenation process is selected such that essentially all highly unsaturated hydrocarbon such as alkyne (e.g., acetylene) is hydrogenated to its corresponding less unsaturated hydrocarbon such as alkene (e.g., ethylene) thereby removing the alkyne from the product stream while only an insignificant amount of alkene is hydrogenated to a saturated hydrocarbon such as alkane (e.g., ethane). Such selective hydrogenation process minimizes the loss of desired less unsaturated hydrocarbons and, in the front-end and total cracked gas processes, avoids a "runaway" reaction which is difficult to control, as has been pointed out in the above-identified patents.

It is also generally known to those skilled in the art that impurities, such as carbon monoxide, and sulfur impurities, such $H_2S$, COS, mercaptans and organic sulfides, which are present in an alkyne-containing feed or product stream can poison and deactivate a palladium-containing catalyst. For example, carbon monoxide is well known to temporarily poison or inactivate such hydrogenation catalyst. It is also generally known by those skilled in the art that a sulfur impurity such as a sulfur compound (such as $H_2S$, COS, mercaptans, and organic sulfides), when present during the hydrogenation of highly unsaturated hydrocarbons such as diolefins (alkadienes) or alkynes to less unsaturated hydrocarbons such as monoolefins (alkenes), can poison and deactivate hydrogenation catalysts. This is especially true in a depropanizer hydrogenation process because the feed stream from the depropanizer being sent to the acetylene removal unit (also referred to as "ARU") of such depropanizer hydrogenation process typically contains low levels of a sulfur compound(s) with the possibility of transient spikes in the level of such sulfur compound(s). Thus, the development of a catalyst composition and its use in processes for the hydrogenation of highly unsaturated hydrocarbons such as diolefins (alkadienes) or alkynes to less unsaturated hydrocarbons such as monoolefins (alkenes) in the presence of a sulfur impurity such as a sulfur compound would also be a significant contribution to the art and to the economy.

A palladium-containing "skin" catalyst in which palladium is distributed on the surface or "skin" of the catalyst has been developed which is known to be more selective and active than a non-skin catalyst in converting acetylene in an ethylene stream to ethylene. See for example, U.S. Pat. No. 4,484,015. It is known that the catalyst selectivity is determined, in part, by the skin thickness. Generally, catalyst selectivity decreases as the skin thickness increases. There is therefore an ever-increasing need to develop a catalyst having a better "skin" on the catalyst for a better selective hydrogenation of a highly unsaturated hydrocarbon, such as an alkyne, to a less unsaturated hydrocarbon, such as an alkene, without further hydrogenation to a saturated hydrocarbon, such as an alkane.

Palladium supported on alumina has been successfully used in dry hydrogenation processes for many years. However, in some processes such as the so-called "total cracked gas" process in which the steam is not removed from the olefins stream, the selective hydrogenation of a highly unsaturated hydrocarbon, such as an alkyne, to a less unsaturated hydrocarbon, such as an alkene, must be accomplished in the presence of steam. In such process(es), the alumina supported catalyst may have a much shorter life because alumina is not stable in steam. Therefore, there is also an increasing need to develop a palladium-containing catalyst on a steam-stable support.

As such, development of an improved palladium catalyst and a process therewith in the selective hydrogenation of a highly unsaturated hydrocarbon, such as an alkyne, to a less unsaturated hydrocarbon, such as an alkene, in the presence of an impurity would be a significant contribution to the art and to the economy.

It is also generally known that catalysts having a metal aluminate support, such as a zinc aluminate support, can be used in the selective hydrogenation and dehydrogenation of hydrocarbons. In general, prior art processes to produce such metal aluminate support typically involve physically mixing a metal component, such as metal oxide, and an aluminum component, such as aluminum oxide, followed by drying and calcining to produce a metal aluminate catalyst support containing a metal aluminate such as a zinc aluminate, also referred to as a zinc spinel. Another common process of producing such metal aluminate catalyst support comprises coprecipitating an aqueous solution of a metal component, such as metal nitrate, and an aqueous solution of an aluminum component, such as aluminum nitrate, followed by drying and calcining such as the process disclosed in U.S. Pat. No. 3,641,182. However, these processes are costly and time-consuming. Consequently, a process to produce a metal aluminate catalyst support, which does not involve physical mixing or coprecipitation, which can be incorporated with palladium and a catalyst component comprising either silver, an alkali metal compound, or both silver and an alkali metal compound, and which can be used in the selective hydrogenation of a highly unsaturated hydrocarbon, such as an alkyne, to a less unsaturated hydrocarbon, such as an alkene, in the presence of an impurity would also be of significant contribution to the art and to the economy.

SUMMARY OF THE INVENTION

An object of this invention is to provide a catalyst composition that can be used for selectively hydrogenating a highly unsaturated hydrocarbon, such as an alkyne, to a less unsaturated hydrocarbon, such as an alkene. Such catalyst composition can be useful as a catalyst in the hydrogenation of a highly unsaturated hydrocarbon such as a diolefin and/or alkyne to a less unsaturated hydrocarbon such as a monoolefin.

Another object of this invention is to provide a palladium-containing catalyst composition wherein the palladium is better distributed on the skin of the catalyst composition, as compared to known "skin" catalysts.

Yet another object of the present invention is to provide a catalyst composition which comprises a metal aluminate catalyst support wherein such metal aluminate catalyst support is prepared by a process that does not involve the physical mixing of a metal component and an aluminum component.

Still another object of the present invention is to provide a catalyst composition which comprises a metal aluminate catalyst support wherein such metal aluminate catalyst support is prepared by a process that does not involve a coprecipitation of a metal component and an aluminum component.

A further object of the present invention is to provide a catalyst composition which comprises a metal aluminate catalyst support which is prepared by a process that is economically cheaper and easier than a method(s) other than the inventive process(es) disclosed herein or prior art methods.

A still further object of the present invention is to provide a method of making such catalyst composition and to provide a process of using such catalyst composition to hydrogenate a highly unsaturated hydrocarbon, such as an alkyne, to a less unsaturated hydrocarbon, such as an alkene, without further hydrogenation to a saturated hydrocarbon, such as an alkane.

A yet further object of this invention is to employ this catalyst composition in the hydrogenation of a highly unsaturated hydrocarbon such as a diolefin or an alkyne to a less unsaturated hydrocarbon. An advantage of this invention is that there is an increased or enhanced selectivity to a desired product such as a less unsaturated hydrocarbon compared to a catalyst composition prepared by methods other than the inventive process(es) disclosed herein.

According to a first embodiment of this invention, a catalyst composition is provided which can be used for selectively hydrogenating a highly unsaturated hydrocarbon such as, for example, an alkyne or a diolefin. The catalyst composition comprises palladium, an inorganic support material comprising a metal aluminate (i.e., a metal aluminate catalyst support), and a catalyst component comprising either silver or an alkali metal compound, or both silver and an alkali metal compound. Such metal aluminate catalyst support is prepared by a process which comprises incorporating alumina with a metal component, preferably impregnating alumina with a melted metal component, to thereby provide a metal-incorporated alumina followed by drying and high temperature calcining to thereby provide a metal aluminate catalyst support. Such metal aluminate catalyst support contains a metal aluminate similar to those metal aluminate catalyst supports produced by physically mixing a metal component, such as metal oxide, and an aluminum component, such as aluminum oxide, or coprecipitating a metal-containing solution and an aluminum-containing solution, followed by drying and calcining.

According to a second embodiment of this invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition, under a condition sufficient to effect a selective hydrogenation of the highly unsaturated hydrocarbon. The catalyst composition can be the same as the catalyst composition disclosed in the first embodiment of this invention.

Other objects and advantages of the invention will be apparent from the detailed description of the invention and the appended claims.

DETAILED DESCRIPTION OF THE INVENTION

As used in the present invention, the term "fluid" denotes gas, liquid, vapor, or combinations thereof. The term "palladium" refers to palladium metal. The term "silver" refers to silver metal. The term "substantial" or "substantially" generally means more than trivial. The term "saturated hydrocarbon" refers to any hydrocarbon which does not contain any carbon-to-carbon double bonds or carbon-to-carbon triple bonds. Examples of saturated hydrocarbons include, but are not limited to, ethane, propane, butanes, pentanes, hexanes, octanes, decanes, naphtha, and the like and combinations thereof.

The term "highly unsaturated hydrocarbon" refers to a hydrocarbon having a triple bond or two or more double bonds between carbon atoms in the molecule. Examples of highly unsaturated hydrocarbons include, but are not limited to, aromatic compounds such as benzene and naphthalene; alkynes such as acetylene, propyne (also referred to as methylacetylene), and butynes; diolefins such as propadiene, butadienes, pentadienes (including isoprene), hexadienes, octadienes, and decadienes; and the like and combinations thereof.

The term "less unsaturated hydrocarbon" refers to a hydrocarbon in which the triple bond in the highly unsaturated hydrocarbon is hydrogenated to a double bond or a hydrocarbon in which the number of double bonds is one less, or at least one less, than that in the highly unsaturated hydrocarbon. Examples of less unsaturated hydrocarbons include, but are not limited to, monoolefins such as ethylene, propylene, butenes, pentenes, hexenes, octenes, decenes, and the like and combinations thereof.

The term "hydrogenation process" refers to a process which converts a highly unsaturated hydrocarbon such as an alkyne or a diolefin to a less unsaturated hydrocarbon such as a monoolefin or a saturated hydrocarbon such as an alkane. The term "selective" refers to such hydrogenation process in which a highly unsaturated hydrocarbon such as an alkyne or a diolefin is converted to a less unsaturated hydrocarbon such as a monoolefin without further hydrogenating the less unsaturated hydrocarbon to a saturated hydrocarbon such as an alkane. Thus, for example, when a highly unsaturated hydrocarbon is converted to a less unsaturated hydrocarbon without further hydrogenating such less unsaturated hydrocarbon to a saturated hydrocarbon, the hydrogenation process is "more selective" than when such highly unsaturated hydrocarbon is hydrogenated to a less unsaturated hydrocarbon and then further hydrogenated to a saturated hydrocarbon.

According to the first embodiment of this invention, a catalyst composition which can be used to selectively hydrogenate a highly unsaturated hydrocarbon (such as an alkyne or a diolefin) to a less unsaturated hydrocarbon (such as an alkene or a monoolefin) is provided. The catalyst composition comprises (a) palladium such as palladium metal, palladium oxide, or combinations thereof, (b) a catalyst component comprising silver or an alkali metal compound or both silver and an alkali metal compound, and (c) an inorganic support comprising a metal aluminate wherein the palladium can be present as "skin" on or near the surface of the catalyst composition and the silver or alkali metal compound, or both if present, can be distributed as skin with the palladium or throughout the catalyst composition.

The term "skin" refers to the exterior surface of the catalyst composition which can contain components, such as palladium, of the catalyst composition. The skin can be any thickness as long as such thickness can promote the hydrogenation process(es) disclosed herein. Generally, the thickness of the skin can be in the range of from about 1 micron to about 1000 microns, preferably in the range of from about 5 microns to about 750 microns, more preferably in the range of from about 5 microns to about 500 microns, and most preferably in the range of from 10 microns to 300 microns. Preferably, the palladium is concentrated in the skin of the catalyst composition whereas the catalyst component comprising silver or an alkali metal compound, or both silver and an alkali metal compound, is distributed throughout the catalyst composition.

The catalyst composition hydrogenates more effectively when the skin is relatively thin (such as the most preferable skin thickness of 10 microns to 300 microns) than when then the skin is thicker (such as greater than 300 microns). Thus, there is a significant benefit, better or more selective hydrogenation, by preparing a catalyst composition with a thin skin, rather than a thick skin. Further, there is a significant benefit, better hydrogenation, by preparing a catalyst composition with a skin than a catalyst composition without a skin.

Various skin catalysts have been developed. See for example U.S. Pat. Nos. 4,404,124 and 4,484,015, the disclosures of which are incorporated herein by reference.

One can use any suitable method to determine the concentration of the palladium in the skin of the catalyst composition. Determining the concentration of the palladium in the skin of the catalyst composition also helps in determining the thickness of the skin. One technique currently favored is the electron microprobe which is known to one skilled in the art. Another technique involves breaking open a representative sample of the catalyst composition (in catalyst particle form) and treating the catalyst particles with a dilute alcoholic solution of N,N-dimethyl-para-nitrosoaniline. The treating solution reacts with the palladium to give a red color which can be used to evaluate the distribution of the palladium. Another technique for measuring the concentration of the palladium in the skin of the catalyst composition involves breaking open a representative sample of catalyst particles followed by treatment with a reducing agent such as, for example, hydrogen, to change the color of the skin to evaluate the distribution of the palladium.

Generally, palladium can be present in the catalyst composition in any weight percent so long as the palladium is substantially concentrated as skin on or near the surface of the catalyst composition and that such weight percent is effective in selectively hydrogenating a highly unsaturated hydrocarbon (such as an alkyne) to a less unsaturated hydrocarbon (such as an alkene). Generally, the catalyst composition comprises palladium in the range of from about 0.0001 weight percent palladium based on the total weight of the catalyst composition to about 3 weight percent palladium, preferably in the range of from about 0.0005 weight percent palladium to about 1.5 weight percent palladium and, most preferably, in the range of from 0.001 weight percent palladium to 1.0 weight percent palladium.

Examples of suitable palladium compounds which can be used for incorporating the palladium of such palladium compounds into, onto, or with an inorganic support include, but are not limited to, palladium bromide, palladium chloride, palladium iodide, palladium nitrate, palladium nitrate hydrate, tetraamine palladium nitrate, palladium oxide, palladium oxide hydrate, palladium sulfate, and the like and combinations thereof. The palladium can have any available oxidation state. The presently preferred palladium compound is palladium chloride. Most preferably, hydrochloric acid is added to such palladium chloride ($PdCl_2$) to form a $PdCl_4^{-2}$ complex. Excess hydrochloric acid should be avoided. When added to the support by impregnation from solution, some of the compounds can be added from aqueous solution, but others will require non-aqueous solvents such as alcohols, hydrocarbons, ethers, ketones and the like.

The catalyst composition can additionally comprise a catalyst component comprising silver. Silver can be present in the catalyst composition in any weight percent as long as such weight percent is effective in selectively hydrogenating a highly unsaturated hydrocarbon (such as an alkyne) to a less unsaturated hydrocarbon (such as an alkene). Generally, the catalyst composition comprises silver in the range of from about 0.0003 weight percent silver based on the total weight of the catalyst composition to about 20 weight percent silver, preferably in the range of from about 0.003 weight percent silver to about 10 weight percent silver and, most preferably, in the range of from 0.003 weight percent silver to 5 weight percent silver. Generally, the weight ratio of silver to palladium (Ag:Pd weight ratio) in the catalyst composition can be in the range of from about 0.1:1 to about 20:1, preferably in the range of from about 1:1 to about 10:1 and, most preferably, in the range of from 3:1 to 8:1.

Suitable examples of silver compounds for use in incorporating, preferably impregnating, the silver of such silver compound(s) into, onto, or with the inorganic support include, but are not limited to, silver nitrate, silver acetate, silver cyanide and the like and combinations thereof. The presently preferred silver compound is silver nitrate.

In lieu of a catalyst component comprising silver or in addition to silver, the catalyst composition can additionally comprise a catalyst component comprising an alkali metal compound. Any alkali metal-containing compound(s) can be used in the catalyst composition as long as the resulting catalyst composition is effective in selectively hydrogenating a highly unsaturated hydrocarbon (such as an alkyne) to a less unsaturated hydrocarbon (such as an alkene). Suitable examples of alkali metal compounds for use in incorporating, preferably impregnating, the alkali metal compound(s) into, onto, or with the inorganic support generally include, but are not limited to, alkali metal halides, alkali metal hydroxides, alkali metal carbonates, alkali metal bicarbonates, alkali metal nitrates, alkali metal carboxylates, and the like and combinations thereof. Preferably, the alkali metal compound is an alkali metal halide, more preferably the alkali metal compound is an alkali metal iodide or an alkali metal fluoride. Generally, the alkali metal of such alkali metal compound is selected from the group consisting of potassium, rubidium, cesium, and the like and combinations thereof. Preferably, the alkali metal of such alkali metal compound is potassium. Preferably, the alkali metal compound is potassium iodide (KI) and, more preferably, the alkali metal compound is potassium fluoride (KF).

Further examples of suitable alkali metal compounds include sodium fluoride, potassium fluoride, lithium fluoride, rubidium fluoride, cesium fluoride, sodium iodide, potassium iodide, lithium iodide, rubidium iodide, cesium iodide, sodium chloride, potassium chloride, lithium chloride, rubidium chloride, cesium chloride, sodium bromide, potassium bromide, lithium bromide, rubidium bromide, cesium bromide, sodium hydroxide, potassium hydroxide, lithium hydroxide, rubidium hydroxide, cesium hydroxide, sodium oxide, potassium oxide, lithium oxide, rubidium oxide, cesium oxide, sodium carbonate, potassium carbonate, lithium carbonate, rubidium carbonate, cesium carbonate, sodium nitrate, potassium nitrate, lithium nitrate, rubidium nitrate, cesium nitrate, and the like and combinations thereof.

Generally, the catalyst composition comprises alkali metal in the range of from about 0.001 weight percent alkali metal to about 10 weight percent alkali metal based on the total weight of the catalyst composition. Preferably, the catalyst composition comprises alkali metal in the range of from about 0.005 weight percent alkali metal to about 5 weight percent alkali metal and, most preferably, in the range of from 0.01 weight percent alkali metal to 2 weight percent alkali metal. Generally, the weight ratio of alkali metal to palladium is in the range of from about 0.05:1 to about 500:1. Preferably, the weight ratio of alkali metal to palladium is in the range of from about 0.1:1 to about 200:1 and, most preferably, in the range of from 0.2:1 to 100:1.

When the alkali metal compound is an alkali metal iodide, the catalyst composition comprises alkali metal iodide in the range of from about 0.03 weight percent iodine (chemically bound as iodide) (on a total catalyst composition weight basis) to about 10 weight percent iodine. Preferably, the catalyst composition comprises alkali metal iodide in the range of from about 0.1 weight percent iodine to about 5 weight percent iodine and, most preferably, in the range of from 0.2 weight percent iodine to 1 weight percent iodine. Generally, the atomic ratio of iodine to alkali metal is in the range of from about 0.5:1 to about 4:1. Preferably, the atomic ratio of iodine to alkali metal is in the range of from about 1:1 to about 3:1. When the alkali metal compound is an alkali metal iodide, it should be used in lieu of the silver.

When the alkali metal compound is an alkali metal fluoride, the catalyst composition comprises alkali metal fluoride in the range of from about 0.03 weight percent fluorine (chemically bound as fluoride) (on a total catalyst composition weight basis) to about 10 weight percent fluorine. Preferably, the catalyst composition comprises alkali metal fluoride in the range of from about 0.1 weight percent fluorine to about 5 weight percent fluorine and, most preferably, in the range of from 0.2 weight percent fluorine to 1 weight percent fluorine. Generally, the atomic ratio of fluorine to alkali metal is in the range of from about 0.5:1 to about 4:1. Preferably, the atomic ratio of fluorine to alkali metal is in the range of from about 1:1 to about 3:1.

The inorganic support material of this invention comprises a metal aluminate prepared by an inventive process(es) which does not involve the physical mixing of a metal component and an aluminum component and does not involve a coprecipitation of a metal component and an aluminum component. When a catalyst composition comprises an inorganic support material prepared according to the inventive process(es) disclosed herein and additionally comprises palladium and a catalyst component comprising either silver or an alkali metal compound, or both silver and an alkali metal compound, and is utilized in the hydrogenation of a highly unsaturated hydrocarbon to a less unsaturated hydrocarbon, there is an increased or enhanced selectivity to a desired product such as a less unsaturated hydrocarbon when compared to a catalyst composition comprising an inorganic support material prepared by methods other than the inventive process(es) disclosed herein.

It has been discovered that a metal aluminate catalyst support can be readily prepared from existing pre-formed alumina (also referred to as aluminum oxide) tablets, pellets, extrudates, spheres, and the like and combinations thereof by incorporating, preferably impregnating, such alumina with a metal component, preferably a melted metal component, followed by drying, and then high temperature calcining. The resulting metal aluminate catalyst support contains a metal aluminate such as a zinc aluminate, also referred to as a zinc spinel, which is readily formed on the outside of, i.e., on the surface of, the alumina. Such metal aluminate catalyst support preparation is considerably cheaper and easier than preparation techniques involving physically mixing a metal component, such as metal oxide, and an aluminum component, such as aluminum oxide, or coprecipitating metal-containing and aluminum-containing solutions, followed by extended calcining and then pelletizing and/or extruding to form catalyst pellets or granules.

Generally, the alumina used in producing the metal aluminate catalyst support according to the inventive process(es) disclosed herein can be any suitable alumina such as, but not limited to, alpha alumina, beta alumina, delta alumina, eta alumina, gamma alumina, and the like and combinations thereof. Preferably, such alumina is gamma alumina. The alumina can also contain minor amounts of other ingredients, such as, for example, silica in a range of from about 1 weight percent silica to about 10 weight percent silica, which do not adversely affect the quality of the metal aluminate catalyst support. Generally, it is desirable to have an essentially pure alumina, preferably essentially pure gamma alumina, as a starting material for preparing the metal aluminate catalyst support. The starting alumina can be made by any manner or method(s) known in the art. As an example, a suitable commercially available starting alumina for use in preparing the metal aluminate catalyst support according to the inventive process(es) described herein are gamma alumina tablets or extrudate pellets or spheres such as those manufactured by UOP Inc., McCook, Ill., and Engelhard Company, Elyria, Ohio.

Alumina suitable for use in the inventive process(es) described herein can also be characterized by having the following characteristics. Generally, the surface area of the alumina is in the range of from about 5 $m^2/g$ (measured by the Brunauer, Emmett, Teller method, i.e. BET method) to about 400 $m^2/g$, preferably in the range of from about 10 $m^2/g$ to about 300 $m^2/g$ and, most preferably, in the range of from 50 $m^2/g$ to 200 $m^2/g$.

The pore volume of the alumina is generally in the range of from about 0.05 mL/g to about 2 mL/g, preferably in the range of from about 0.10 nmL/g to about 1.5 mL/g and, most preferably, in the range of from 0.20 mL/g to 1 mL/g.

The average pore diameter of the alumina is generally in the range of from about 5 angstroms to about 600 angstroms, preferably in the range of from about 10 angstroms to about 500 angstroms and, most preferably, in the range of from 25 angstroms to 200 angstroms.

The alumina can have any suitable shape or form. Preferably such alumina is in the form of tablets, pellets, extrudates, spheres, and the like and combinations thereof. The alumina generally has a particle size in the range of from about 0.5 millimeters (mm) to about 10 mm, preferably in the range of from about 1 mm to about 8 mm and, most preferably, in the range of from 1 mm to 6 mm.

Any metal component which can form a spinel when utilized in accordance with the inventive process(es) disclosed herein can be used. Examples of a potentially suitable metal component for incorporating the metal of such metal component, preferably impregnating the metal of such metal component into, onto, or with the alumina to thereby provide a metal-incorporated alumina include, but are not limited to, a zinc component, a magnesium component, a calcium component, a barium component, a beryllium component, a cobalt component, an iron component, a manganese component, a strontium component, a lithium component, a potassium component, and the like and combinations thereof. Preferable examples of a potentially suitable metal component for incorporating the metal of such metal component, preferably impregnating the metal of such metal component into, onto, or with the alumina to thereby provide a metal-incorporated alumina include, but are not limited to, a zinc component, a magnesium component, a calcium component, and the like and combinations thereof. More preferably, such metal component is a zinc component.

Examples of a potentially suitable zinc component for incorporating zinc, preferably impregnating zinc into, onto, or with the alumina include, but are not limited to, zinc nitrate hexahydrate, zinc nitrate, hydrated zinc nitrate, zinc chloride, zinc acetate dihydrate, zinc acetylacetonate hydrate, zinc carbonate hydroxide monohydrate, zinc perchlorate hexahydrate, hydrated zinc sulfate, zinc sulfate monohydrate, zinc sulfate heptahydrate, and the like and combinations thereof. The preferred zinc component for incorporating zinc, preferably impregnating zinc into, onto, or with the alumina is hydrated zinc nitrate. The most preferred zinc component for incorporating zinc, preferably impregnating zinc into, onto, or with the alumina is zinc nitrate hexahydrate.

Examples of a potentially suitable magnesium component for incorporating magnesium, preferably impregnating magnesium into, onto, or with the alumina include, but are not limited to, magnesium nitrate hexahydrate, magnesium nitrate, hydrated magnesium nitrate, magnesium chloride, hydrated magnesium chloride, magnesium chloride hexahydrate, magnesium acetate tetrahydrate, magnesium acetylacetonate dihydrate, magnesium carbonate hydroxide pentahydrate, magnesium perchlorate, magnesium perchlorate hexahydrate, magnesium sulfate, magnesium sulfate heptahydrate, magnesium sulfate monohydrate, and the like and combinations thereof. The preferred magnesium component for incorporating magnesium, preferably impregnating magnesium into, onto, or with the alumina is hydrated magnesium nitrate. The most preferred magnesium component for incorporating magnesium, preferably impregnating magnesium into, onto, or with the alumina is magnesium nitrate hexahydrate.

Examples of a potentially suitable calcium component for incorporating calcium, preferably impregnating calcium into, onto, or with the alumina include, but are not limited to, calcium nitrate tetrahydrate, calcium nitrate, hydrated calcium nitrate, calcium chloride, hydrated calcium chloride, calcium chloride dihydrate, calcium chloride hexahydrate, calcium chloride hydrate, calcium acetate hydrate, calcium acetate monohydrate, calcium acetylacetonate hydrate, calcium perchlorate tetrahydrate, calcium sulfate, calcium sulfate dihydrate, calcium sulfate hemihydrate, and the like and combinations thereof. The preferred calcium component for incorporating calcium, preferably impregnating calcium into, onto, or with the alumina is hydrated calcium nitrate. The most preferred calcium component for incorporating calcium, preferably impregnating calcium into, onto, or with the alumina is calcium nitrate tetrahydrate.

Examples of a potentially suitable barium component for incorporating barium, preferably impregnating barium into, onto, or with the alumina include, but are not limited to, barium nitrate, hydrated barium nitrate, barium chloride, hydrated barium chloride, barium chloride dihydrate, barium acetate, barium acetylacetonate hydrate, barium carbonate, barium perchlorate, barium perchlorate trihydrate, barium sulfate, and the like and combinations thereof. The preferred barium component for incorporating barium, preferably impregnating barium into, onto, or with the alumina is hydrated barium nitrate. The most preferred barium component for incorporating barium, preferably impregnating barium into, onto, or with the alumina is barium nitrate.

Examples of a potentially suitable beryllium component for incorporating beryllium, preferably impregnating beryllium into, onto, or with the alumina include, but are not limited to, beryllium nitrate trihydrate, hydrated beryllium nitrate, beryllium chloride, hydrated beryllium sulfate, beryllium sulfate tetrahydrate, and the like and combinations thereof. The preferred beryllium component for incorporating beryllium, preferably impregnating beryllium into, onto, or with the alumina is hydrated beryllium nitrate. The most preferred beryllium component for incorporating beryllium, preferably impregnating beryllium into, onto, or with the alumina is beryllium nitrate trihydrate.

Examples of a potentially suitable cobalt component for incorporating cobalt, preferably impregnating cobalt into, onto, or with the alumina include, but are not limited to, cobalt nitrate hexahydrate, hydrated cobalt nitrate, cobalt chloride, hydrated cobalt chloride, cobalt chloride hexahydrate, cobalt chloride hydrate, cobalt acetate tetrahydrate, cobalt acetylacetonate, cobalt acetylacetonate hydrate, cobalt carbonate hydrate, cobalt perchlorate hexahydrate, hydrated cobalt sulfate, cobalt sulfate hydrate, and the like and combinations thereof. The preferred cobalt component for incorporating cobalt, preferably impregnating cobalt into, onto, or with the alumina is hydrated cobalt nitrate. The most preferred cobalt component for incorporating cobalt, preferably impregnating cobalt into, onto, or with the alumina is cobalt nitrate hexahydrate.

Examples of a potentially suitable iron component for incorporating iron, preferably impregnating iron into, onto, or with the alumina include, but are not limited to, iron nitrate nonahydrate, hydrated iron nitrate, iron chloride, hydrated iron chloride, iron chloride tetrahydrate, iron chloride hexahydrate, iron acetate, iron acetylacetonate, iron perchlorate hexahydrate, hydrated iron sulfate, iron sulfate heptahydrate, and the like and combinations thereof. The preferred iron component for incorporating iron, preferably impregnating iron into, onto, or with the alumina is hydrated iron nitrate. The most preferred iron component for incorporating iron, preferably impregnating iron into, onto, or with the alumina is iron nitrate nonahydrate.

Examples of a potentially suitable manganese component for incorporating manganese, preferably impregnating manganese into, onto, or with the alumina include, but are not limited to, manganese nitrate hexahydrate, hydrated manganese nitrate, manganese nitrate hydrate, manganese chloride, hydrated manganese chloride, manganese chloride tetrahydrate, manganese acetate dihydrate, manganese acetate tetrahydrate, manganese acetylacetonate, manganese carbonate, manganese perchlorate hexahydrate, hydrated manganese sulfate, manganese sulfate monohydrate, and the like and combinations thereof The preferred manganese component for incorporating manganese, preferably impregnating manganese into, onto, or with the alumina is hydrated manganese nitrate. The most preferred manganese component for incorporating manganese, preferably impregnating manganese into, onto, or with the alumina is manganese nitrate hexahydrate.

Examples of a potentially suitable strontium component for incorporating strontium, preferably impregnating strontium into, onto, or with the alumina include, but are not limited to, strontium nitrate, hydrated strontium nitrate, strontium chloride, hydrated strontium chloride, strontium chloride hexahydrate, strontium acetate, strontium acetylacetonate, strontium carbonate, strontium perchlorate hydrate, hydrated strontium sulfate, strontium sulfate, and the like and combinations thereof. The preferred strontium component for incorporating strontium, preferably impregnating strontium into, onto, or with the alumina is strontium nitrate.

Examples of a potentially suitable lithium component for incorporating lithium, preferably impregnating lithium into, onto, or with the alumina include, but are not limited to, lithium nitrate, hydrated lithium nitrate, lithium chloride, hydrated lithium chloride, lithium chloride hydrate, lithium acetate dihydrate, lithium acetylacetonate, lithium perchlorate, lithium perchlorate trihydrate, lithium sulfate, lithium sulfate monohydrate, and the like and combinations thereof. The preferred lithium component for incorporating lithium, preferably impregnating lithium into, onto, or with the alumina is lithium nitrate.

Examples of a potentially suitable potassium component for incorporating potassium, preferably impregnating potassium into, onto, or with the alumina include, but are not limited to, potassium nitrate, hydrated potassium nitrate, potassium chloride, hydrated potassium chloride, potassium acetylacetonate hemihydrate, potassium carbonate sesquihydrate, potassium perchlorate, potassium sulfate, and the like and combinations thereof. The preferred potassium component for incorporating potassium, preferably impregnating potassium into, onto, or with the alumina is potassium nitrate.

The metal component(s) may be incorporated into, onto, or with the alumina by any suitable means or method(s) for incorporating the metal of such metal component(s) into, onto, or with a substrate material, such as alumina, which results in the formation of a metal-incorporated alumina which can then be dried and calcined to thereby provide a metal aluminate catalyst support. Examples of means or method(s) for incorporating include, but are not limited to, impregnating, soaking, spraying, and the like and combinations thereof. A preferred method of incorporating is impregnating using any standard incipient wetness impregnation technique (i.e., essentially completely filling the pores of the substrate material with a solution of the incorporating elements) for impregnating an alumina substrate with a metal component. A preferred method uses an impregnating solution comprising the desirable concentration of metal component so as to ultimately provide a metal-incorporated, preferably metal-impregnated, alumina which can then be subjected to drying and high temperature calcining to produce a metal aluminate catalyst support.

It can be desirable to use an aqueous solution of a metal component for the impregnation of the alumina. A preferred impregnating solution comprises an aqueous solution formed by dissolving a metal component, preferably such metal component is in the form of a metal salt, such as, but not limited to, a metal chloride, a metal nitrate, a metal sulfate, and the like and combinations thereof, in a solvent, such as, but not limited to, water, alcohols, esters, ethers, ketones, and the like and combinations thereof.

A preferred impregnating solution is formed by dissolving a metal component (such as zinc nitrate hexahydrate, magnesium nitrate hexahydrate, calcium nitrate tetrahydrate, barium nitrate, beryllium nitrate trihydrate, cobalt nitrate hexahydrate, iron nitrate nonahydrate, manganese nitrate hexahydrate, strontium nitrate, lithium nitrate, potassium nitrate, preferably, zinc nitrate hexahydrate) in water. It is acceptable to use somewhat of an acidic solution to aid in the dissolution of the metal component. It is preferred for the alumina to be impregnated with a zinc component by use of a solution containing zinc nitrate hexahydrate dissolved in water. In addition, magnesium nitrate hexahydrate or calcium nitrate tetrahydrate or barium nitrate or beryllium nitrate trihydrate or cobalt nitrate hexahydrate or iron nitrate nonahydrate or manganese nitrate hexahydrate or strontium nitrate or lithium nitrate or potassium nitrate can be used in place of zinc nitrate hexahydrate to impregnate the alumina with the metal of the respective metal component(s).

A more preferred method for incorporating a metal of a metal component into, onto, or with the alumina is to impregnate such alumina with a metal component which has been melted under a melting condition as described herein. Preferably such metal component is in the form of a metal salt, such as, but not limited to, a metal chloride, a metal nitrate, a metal sulfate, and the like and combinations thereof (such as, but not limited to, zinc nitrate hexahydrate, magnesium nitrate hexahydrate, calcium nitrate tetrahydrate, barium nitrate, beryllium nitrate trihydrate, cobalt nitrate hexahydrate, iron nitrate nonahydrate, manganese nitrate hexahydrate, strontium nitrate, lithium nitrate, potassium nitrate, and the like and combinations thereof, preferably, zinc nitrate hexahydrate). Addition of small amounts of an aqueous medium such as water to the metal component can be used to assist in the melting of such metal component.

Such melting condition includes a temperature below the decomposition temperature of the metal component for a time period and at a pressure that provides for a melted metal component, preferably a pourable melted metal component. The term "decomposition temperature" refers to the temperature at which the metal component is no longer soluble and is no longer suitable for incorporating, preferably impregnating, the metal of such metal component into, onto, or with alumina according to the inventive process(es) disclosed herein. The term "pourable melted metal component" refers to a metal component that has been subjected to a melting condition and has become viscous enough to pour.

The temperature below the decomposition temperature of the metal component varies depending on the metal component but such temperature should be such as to provide a melted metal component. Such temperature is generally in the range of from about 25° C. to about 160° C., preferably in the range of from about 30° C. to about 150° C., more preferably in the range of from about 35° C. to about 140° C. and, most preferably, in the range of from 35° C. to 130° C.

Such melting condition can include a time period generally in the range of from about 1 minute to about 2 hours, preferably in the range of from about 5 minutes to about 1.5 hours and, most preferably, in the range of from 5 minutes to 1 hour. Such melting condition can include a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained.

The thus-melted metal component is then used to incorporate, preferably impregnate, the metal of such melted metal component into, onto, or with the alumina. The metal of such melted metal component is incorporated, preferably impregnated, into, onto, or with the alumina by adding such melted metal component to the alumina by pouring such melted metal component onto the surface of the alumina by any manner or method(s) which results in substantially all the surface area of the alumina being coated with the melted metal component. Preferably, such melted metal component is poured over the surface of the alumina while the alumina is under constant stirring or tumbling.

It can be desirable to pre-heat the alumina under a heating condition before such melted metal component is poured over the surface of the alumina. Such heating condition can include a temperature generally in the range of from about 80° C. to about 150° C., preferably in the range of from about 85° C. to about 140° C. and, most preferably, in the range of from 90° C. to 130° C. Such heating condition can include a time period generally in the range of from about 1 minute to about 2 hours, preferably in the range of from about 5 minutes to about 1.5 hours and, most preferably, in the range of from 5 minutes to 1 hour. Such heating condition can include a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained. The metal-incorporated, preferably metal-impregnated, alumina can be further heated near the melting point of the metal component for a time period in the range of from about 0.5 hour to about 15 hours, preferably in the range of from about 1 hour to about 8 hours and, most preferably, in the range of from 1 hour to 5 hours.

In a most preferred method, melted zinc nitrate hexahydrate is used to incorporate, preferably impregnate, the zinc of such melted zinc nitrate hexahydrate into, onto, or with the alumina. The zinc of such melted zinc nitrate hexahydrate is incorporated, preferably impregnated, into, onto, or with the alumina by adding such melted zinc nitrate hexahydrate to the alumina by pouring such melted zinc nitrate hexahydrate onto the surface of the alumina by any manner or method(s) which results in substantially all the surface area of the alumina being coated with the melted zinc nitrate hexahydrate. Preferably, such melted zinc nitrate hexahydrate is poured over the surface of the alumina while the alumina is under constant stirring or tumbling. In addition, magnesium nitrate hexahydrate or calcium nitrate tetrahydrate or barium nitrate or beryllium nitrate trihydrate or cobalt nitrate hexahydrate or iron nitrate nonahydrate or manganese nitrate hexahydrate or strontium nitrate or lithium nitrate or potassium nitrate can be used in place of zinc nitrate hexahydrate to incorporate, preferably impregnate, the metal of such metal component(s) into, onto, or with the alumina in the same above-described manner as for incorporating, preferably impregnating, the zinc of such zinc nitrate hexahydrate.

Generally, the amount of metal component, preferably zinc component, incorporated, preferably impregnated, into, onto, or with the alumina is an amount which provides, after the metal-incorporated alumina has been dried and calcined according to the inventive process(es) disclosed herein, a metal aluminate catalyst support having an amount of metal aluminate generally in the range of from about 1 weight percent of the total weight of the metal aluminate catalyst support to about 100 weight percent. Preferably the amount of metal in, on, or with the metal-incorporated alumina is in an amount which provides a metal aluminate catalyst support having an amount of metal aluminate in the range of from about 15 weight percent of the total weight of the metal aluminate catalyst support to about 75 weight percent and, most preferably, in the range of from 25 weight percent to 65 weight percent.

The metal-incorporated alumina can then be dried under a drying condition. Generally, such drying condition can include a temperature in the range of from about 80° C. to about 140° C., preferably in the range of from about 90° C. to about 130° C. and, most preferably, in the range of from 100° C. to 120° C. Such drying condition can also include a time period for drying the metal-incorporated alumina generally in the range of from about 0.5 hour to about 60 hours, preferably in the range of from about 1 hour to about 40 hours and, most preferably, in the range of from 1.5 hours to 20 hours to produce a dried metal-incorporated alumina. Such drying condition can also include a pressure generally in the range of from about atmospheric (i.e., about 14.7 pounds per square inch absolute) to about 150 pounds per square inch absolute (psia), preferably in the range of from about atmospheric to about 100 psia, most preferably about atmospheric, so long as the desired temperature can be maintained. Any drying method(s) known to one skilled in the art such as, for example, air drying, heat drying, and the like and combinations thereof can be used.

The thus-dried metal-incorporated alumina can then be calcined under a calcining condition to thereby provide a metal aluminate catalyst support. The calcining condition is important in providing a metal aluminate catalyst support having physical characteristics, such as, for example, a surface area, pore volume, average pore diameter, and crystalline domain size, in the ranges as disclosed herein, suitable for using such metal aluminate catalyst support as a support for hydrogenation and dehydrogenation catalysts.

Generally, such calcining condition can include a temperature in the range of from about 600° C. to about 1350° C., preferably in the range of from about 675° C. to about 1300° C., more preferably, in the range of from about 800° C. to about 1250° C. and, most preferably, in the range of from 900° C. to 1200° C. Such calcining condition can also include a pressure, generally in the range of from about 7 pounds per square inch absolute (psia) to about 750 psia, preferably in the range of from about 7 psia to about 450 psia and, most preferably, in the range of from 7 psia to 150 psia, and a time period in the range of from about 1 hour to about 60 hours, preferably for a time period in the range of from about 2 hours to about 20 hours and, most preferably, for a time period in the range of from 3 hours to 15 hours.

Upon calcination of the dried metal-incorporated alumina, a metal aluminate will form in, on the outside surface of, or on, but not limited to, the surface of, the alumina to thereby provide a metal aluminate catalyst support of the invention. Examples of a suitable metal aluminate include, but are not limited to, a zinc aluminate, also referred to as a zinc spinel, a magnesium aluminate, also referred to as a magnesium spinel, a calcium aluminate, also referred to as a calcium spinel, a barium aluminate, also referred to as a barium spinel, a beryllium aluminate, also referred to as a beryllium spinel, a cobalt aluminate, also referred to as a cobalt spinel, an iron aluminate, also referred to as an iron spinel, a manganese aluminate, also referred to as a manganese spinel, a strontium aluminate, also referred to as a strontium spinel, a lithium aluminate, also referred to as a lithium spinel, a potassium aluminate, also referred to as a potassium spinel, and the like and combinations thereof. A preferred metal aluminate is selected from the group consisting of a zinc aluminate, also referred to as a zinc spinel, a magnesium aluminate, also referred to as a magnesium spinel, a calcium aluminate, also referred to as a calcium spinel, and the like and combinations thereof. A more preferred metal aluminate is a zinc aluminate, also referred to as a zinc spinel.

The amount of metal aluminate of the metal aluminate catalyst support, preferably zinc aluminate catalyst support, is generally in the range of from about 1 weight percent based on the total weight of the metal aluminate catalyst support to about 100 weight percent. Preferably, the amount of metal aluminate of the metal aluminate catalyst support of the invention is in the range of from about 15 weight percent based on the total weight of the metal aluminate catalyst support to about 75 weight percent and, most preferably, in the range of from 25 weight percent to 65 weight percent.

The amount of alpha alumina of the metal aluminate catalyst support, preferably zinc aluminate catalyst support, is generally in the range of from about 0 weight percent based on the total weight of the metal aluminate catalyst support to about 99 weight percent, preferably in the range of from about 10 weight percent to about 85 weight percent and, most preferably, in the range of from 15 weight percent to 70 weight percent. The crystalline domain size of the alpha alumina of the metal aluminate catalyst support is generally in the range of from about 25 angstroms to about 3000 angstroms, preferably in the range of from about 25 angstroms to about 2500 angstroms and, most preferably, in the range of from 50 angstroms to 2000 angstroms. The "crystalline domain size" is determined from the line broadening of the X-ray diffraction profile.

The amount of gamma alumina of the metal aluminate catalyst support, preferably zinc aluminate catalyst support, generally ranges upwardly from about 0 weight percent based on the total weight of the metal aluminate catalyst support to about 60 weight percent, preferably in the range of from about 0 weight percent to about 50 weight percent and, most preferably, in the range of from 0 weight percent to 40 weight percent.

Generally, the surface area of the metal aluminate catalyst support, preferably zinc aluminate catalyst support, is in the range of from about 1 $m^2/g$ (measured by the Brunauer, Emmett, Teller method, i.e. BET method) to about 200 $m^2/g$, preferably in the range of from about 1 $m^2/g$ to about 150 $m^2/g$, more preferably in the range of from about 5 $m^2/g$ to about 125 $m^2/g$ and, most preferably, in the range of from 10 $m^2/g$ to 80 $m^2/g$.

The pore volume of the metal aluminate catalyst support, preferably zinc aluminate catalyst support, is generally in the range of from about 0.05 mL/g to about 2 mL/g, preferably in the range of from about 0.10 mL/g to about 1.5 mL/g and, most preferably, in the range of from 0.10 mL/g to 1 mL/g.

The average pore diameter of the metal aluminate catalyst support, preferably zinc aluminate catalyst support, is generally in the range of from about 50 angstroms to about 1000 angstroms, preferably in the range of from about 50 angstroms to about 750 angstroms and, most preferably, in the range of from 50 angstroms to 450 angstroms.

The crystalline domain size of the metal aluminate, preferably zinc aluminate, of the metal aluminate catalyst support is generally in the range of from about 25 angstroms to about 1750 angstroms, preferably in the range of from about 25 angstroms to about 1500 angstroms, more preferably in the range of from about 25 angstroms to about 1250 angstroms and, most preferably, in the range of from 25 angstroms to 1000 angstroms.

The particle size of the metal aluminate catalyst support, preferably zinc aluminate catalyst support, is generally in the range of from about 0.5 millimeter (mm) to about 10 mm, preferably in the range of from about 1 mm to about 8 mm and, most preferably, in the range of from 1 mm to 6 mm.

The catalyst composition can be fresh or it can be a used and thereafter oxidatively regenerated catalyst composition. The catalyst composition can have any suitable shape such as spherical, cylindrical, trilobal, or combinations thereof. The preferred shape is either spherical or cylindrical. The particles of the catalyst composition generally have a size in the range of from about 0.5 millimeters (mm) to about 10 mm, preferably in the range of from about 1 mm to about 8 mm and, most preferably, in the range of from 1 mm to 6 mm. Generally, the surface area of the catalyst composition is in the range of from about 1 $m^2/g$ (measured by the Brunauer, Emmett, Teller method, i.e., BET method) to about 200 $m^2/g$, preferably in the range of from about 1 $m^2/g$ to about 150 $m^2/g$, more preferably in the range of from about 5 $m^2/g$ to about 125 $m^2/g$ and, most preferably, in the range of from 10 $m^2/g$ to 80 $m^2/g$.

The catalyst composition can be prepared by any suitable method(s) or means which results in palladium concentrated in the exterior surface skin of the catalyst composition with a catalyst component comprising silver or an alkali metal compound, or both silver and an alkali metal compound, distributed in the skin or throughout the catalyst composition. Generally, the extent of penetration of the palladium into the skin of the catalyst composition can be controlled by adjustment of the acidity of the palladium-containing solution, used in preparing the catalyst composition, with an acid such as, for example, hydrochloric acid. For example, if the palladium compound is palladium chloride ($PdCl_2$), hydrochloric acid should be added to the palladium-containing solution containing the palladium chloride to form a $PdCl_4^{-2}$ complex. Excess hydrochloric acid should be avoided. The catalyst composition components (a) palladium and/or at least one palladium oxide, and (b) a catalyst component comprising either silver or an alkali metal compound (preferably potassium fluoride), or both silver and an alkali metal compound, can be deposited onto and/or incorporated into or with the inorganic support material (comprising a metal aluminate prepared in accordance with the inventive process(es) disclosed herein) by any suitable means and in any suitable order.

The palladium can be incorporated (e.g., by ion exchange or impregnation) into, onto, or with the inorganic support comprising a metal aluminate. A preferred impregnation utilizes an incipient wetness impregnation technique in which a solution of the incorporating element(s) is used to essentially completely fill the pores of a substrate material (such as an inorganic support). The inorganic support can also be sprayed with an impregnating solution comprising a palladium compound. Generally, the concentration of the palladium compound in the impregnating solution is in the range of from about 0.01 mmol/L to about 5 mol/L. Preferably in the range of from about 0.1 mmol/L to about 2 mol/L. Preferably, the solvent of the impregnating solution is water or an alcohol such as ethanol or mixtures thereof. The weight ratio of the impregnating solution comprising a palladium compound to the inorganic support can be any ratio that can produce the catalyst composition comprising palladium in the weight percent ranges disclosed herein.

For example, a catalyst component comprising silver or an alkali metal compound, or both silver and an alkali metal compound, can be incorporated into the inorganic support material comprising a metal aluminate (prepared in accordance with the inventive process(es) disclosed herein) by impregnation, followed by impregnation with at least one Pd compound (such as $H_2PdCl_4$) to obtain an impregnated material, drying the impregnated material under a composition drying condition as described herein to obtain a dried material, and then heating (calcining) under a composition calcining condition as described herein to obtain a final catalyst composition of this invention.

More preferably, an inorganic support material comprising a metal aluminate (prepared in accordance with the inventive process(es) disclosed herein) is impregnated with at least one Pd compound (such as $H_2PdCl_4$) to obtain a palladium-impregnated material, drying the impregnated material under a composition drying condition as described herein to obtain a dried material, and then heating (calcining) under a composition calcining condition as described herein to thereby obtain a dried and calcined palladium/metal aluminate composition. The palladium/metal aluminate composition can then be contacted with a solution (preferably aqueous) of at least one silver compound, preferably silver nitrate, (i.e., a silver-containing solution) or an alkali metal compound, preferably potassium fluoride, (i.e., an alkali metal compound-containing solution) followed by drying under a composition drying condition as described herein to obtain a dried material, and then heating (calcining) under a composition calcining condition as described herein to thereby obtain a final catalyst composition of this invention having a concentration of silver or alkali metal in the ranges as disclosed herein.

The palladium/metal aluminate composition can be contacted with a solution (preferably aqueous) of a silver compound (i.e., a silver-containing solution) followed by drying under a composition drying condition as described herein to obtain a dried material, and then heating (calcining) under a composition calcining condition as described herein to thereby obtain a palladium/silver/metal aluminate composition. Such palladium/silver/metal aluminate composition can then be contacted with a solution of an alkali metal compound (i.e., an alkali metal compound-containing solution) followed by drying under a composition drying condition as described herein to obtain a dried material, and then heating (calcining) under a composition calcining condition as described herein to thereby obtain a final catalyst composition of this invention having concentrations of silver and alkali metal in the ranges as disclosed herein.

In addition, an alkali metal compound (or an alkali metal compound-containing solution) can be incorporated (e.g., by impregnation or spraying) onto the inorganic support material comprising a metal aluminate before such support is impregnated with a suitable palladium compound (or a palladium-containing solution) and, if desired, with a suitable silver compound (or a silver-containing solution). Alternatively, an alkali metal compound can be incorporated (e.g., by impregnation or spraying) with an inorganic support material comprising a metal aluminate simultaneously with or after the impregnation with a suitable palladium compound. When silver is also present in the catalyst composition, an alkali metal compound can be incorporated with the inorganic support material between the palladium and silver impregnation steps or after the impregnation with palladium and silver compounds.

Also for example, a palladium/silver/metal aluminate composition as described herein can be contacted, preferably impregnated, with an aqueous solution of at least one alkali metal hydroxide and/or at least one alkali metal fluoride (preferably KOH and/or KF), followed by drying under a composition drying condition as described herein and calcining under a composition calcining condition as described herein. At least one "wet-reducing" agent (i.e., one or more than one dissolved reducing agent) can also be present during the contacting of the palladium/silver/metal aluminate composition with at least one alkali metal hydroxide and/or at least one alkali metal fluoride. Non-limiting examples of such "wet-reducing" agents are: hydrazine, an alkali metal borohydride, an aldehyde containing 1–6 carbon atoms per molecule such as formaldehyde, a ketone containing 1–6 carbon atoms per molecule, a carboxylic acid containing 1–6 carbon atoms per molecule such as formic acid or ascorbic acid, a reducing sugar containing an aldehyde or alpha-hydroxyketone group such as dextrose, and the like and combinations thereof.

Also for example, a palladium/silver/metal aluminate composition as described herein can be contacted, preferably impregnated, with a non-alkali metal fluoride (preferably selected from the group consisting of HF, $NH_4F$, $NH_4HF_2$, and the like and combinations thereof, more preferably $NH_4F$) disclosed herein in any suitable manner. The non-alkali metal fluoride (preferably $NH_4F$) can be incorporated together with palladium and an alkali metal compound or a suitable silver compound (or palladium and both an alkali metal compound and a suitable silver compound). Or, the non-alkali metal fluoride can be incorporated after the impregnation of the inorganic support material comprising a metal aluminate with palladium and an alkali metal compound, or palladium and both an alkali metal compound and a suitable silver compound. After the incorporation of palladium, alkali metal, fluoride (and/or silver) compounds into the support material has been completed (as described herein), the thus-obtained material is dried under a composition drying condition as described herein and then calcined under a composition calcining condition as described herein. Optionally, the calcined material can then be reduced with hydrogen gas (preferably at a temperature in the range of from about 30° C. to about 100° C., for a time period in the range of from about 0.5 hour to about 20 hours), so as to reduce oxides of palladium and of silver (if present) to the corresponding metal(s).

Generally, the concentration of a silver compound or an alkali metal compound (preferably an alkali fluoride compound) in the contacting solution (preferably aqueous) is in the range of from about 0.01 mmol/L to about 10 mol/L (preferably in the range of from about 0.1 mmol/L to about 3 mol/L). The preferred silver contacting method is by soaking, i.e., essentially completely filling the pores and the external surface of the inorganic support material comprising a metal aluminate with a silver compound-containing solution. The preferred alkali metal contacting method is "incipient wetness impregnation," i.e., essentially completely filling the pores of the inorganic support material comprising a metal aluminate with an alkali metal compound-containing solution (preferably an alkali fluoride-containing solution). Generally, the weight ratio of a silver-containing compound solution or an alkali metal compound-containing solution to the inorganic support material can be any ratio that can produce a catalyst composition having a concentration of silver or alkali metal, or both silver and alkali metal, in the ranges disclosed herein. The impregnated material can then be dried under a composition drying condition as described herein followed by calcining under a composition calcining condition as described herein to obtain the final catalyst composition.

Generally a composition drying condition, as referred to herein, includes a temperature in the range of from about 35° C. to about 160° C., preferably in the range of from about 40° C. to about 155° C. and, most preferably, in the range of from 45° C. to 150° C. Such composition drying condition includes a time period for conducting such drying generally in the range of from about 0.5 hour to about 6 hours, preferably in the range of from about 1 hour to about 5 hours and, most preferably, in the range of from 1.5 hours to 4 hours. Such composition drying condition includes a pressure in the range of from about atmospheric (i.e., about 14.7 pounds per square inch absolute) to about 100 pounds per square inch absolute (psia), preferably about atmospheric.

Generally a composition calcining condition, as referred to herein, includes calcining of the composition either in air or in a non-oxidizing gas atmosphere at a temperature in the range of from about 200° C. to about 800° C., preferably at a temperature in the range of from about 250° C. to about 600° C. and, most preferably, at a temperature in the range of from 350° C. to 550° C. Such composition calcining condition generally includes a time period in the range of from about 0.5 hour to about 40 hours, preferably for a time period in the range of from about 0.75 hour to about 30 hours and, most preferably, for a time period in the range of from 1 hour to 20 hours. Such composition calcining condition generally includes a pressure in the range of from about 7 pounds per square inch absolute (psia) to about 750 psia, preferably in the range of from about 7 psia to about 450 psia and, most preferably, in the range of from 7 psia to 150 psia.

According to the second embodiment of this invention, a hydrogenation process is provided. The hydrogenation process of this invention can comprise contacting a hydrocarbon-containing fluid which comprises one or more highly unsaturated hydrocarbon(s) such as an aromatic hydrocarbon(s), alkyne(s), and/or diolefin(s) with the catalyst composition disclosed herein in the presence of hydrogen in a hydrogenation zone under a hydrogenation condition to hydrogenate such one or more highly unsaturated hydrocarbon(s) to a less unsaturated hydrocarbon such as a monoolefin. The highly unsaturated hydrocarbon(s) is present in the hydrocarbon-containing fluid as an impurity generally at a level found in typical commercial feed streams. The highly unsaturated hydrocarbon(s) is present in the hydrocarbon-containing fluid generally in the range of from about 1 part by weight highly unsaturated hydrocarbon(s) per billion parts by weight hydrocarbon-containing fluid (i.e., about 1 ppb) to about 50 parts by weight highly unsaturated hydrocarbon(s) per 500 parts by weight hydrocarbon-containing fluid (i.e., about 10 weight percent), typically at a level in the range of from about 10 ppb to about 5 weight percent and, most typically, at a level in the range of from 100 ppb to 1 weight percent.

Hydrogen can be present either in the hydrocarbon-containing fluid or in a hydrogen-containing fluid which is mixed with the hydrocarbon-containing fluid before contacting with the catalyst composition disclosed herein. If a hydrogen-containing fluid is used, it can be a substantially pure hydrogen or any fluid containing a sufficient concentration of hydrogen to effect the hydrogenation disclosed herein. It can also contain other gases such as, for example, nitrogen, methane, carbon monoxide, carbon dioxide, steam, or combinations thereof so long as the hydrogen-containing fluid contains a sufficient concentration of hydrogen to effect the hydrogenation disclosed herein.

Optionally, the catalyst can be first treated, prior to the hydrogenation disclosed herein, with a hydrogen-containing fluid to activate the catalyst composition. Such reductive, or activation, treatment can be carried out at a temperature generally in the range of from about 20° C. to about 200° C., preferably in the range of from about 25° C. to about 150° C. and, most preferably, in the range of from 30° C. to 125° C. for a time period in the range of from about 1 minute to about 30 hours, preferably in the range of from about 0.5 hour to about 25 hours and, most preferably, in the range of from 1 hour to 20 hours at a pressure generally in the range of from about 1 pound per square inch absolute to about 1000 pounds per square inch absolute (psia), preferably in the range of from about 14.7 psia to about 500 psia and, most preferably, in the range of from 60 psia to 200 psia. During this reductive treatment, palladium and silver compounds (primarily oxides) which may be present in the catalyst composition after the composition drying step and the composition calcining step described herein are substantially reduced to palladium and silver. When this optional reductive treatment is not carried out, the hydrogen gas present in the reaction medium accomplishes this reduction of oxides of palladium and silver during the initial phase of the selective hydrogenation reaction(s) of this invention.

The hydrocarbon-containing fluid of the hydrogenation process(es) of this invention can also comprise one or more less unsaturated hydrocarbon(s) such as a monoolefin(s) and one or more saturated hydrocarbon(s) such as an alkane(s). These additional hydrocarbons can be present in the hydrocarbon-containing fluid at a level in the range of from about 0.001 weight percent to about 99.999 weight percent.

Examples of suitable alkynes include, but are not limited to, acetylene, propyne (also referred to as methylacetylene), 1-butyne, 2-butyne, 1-pentyne, 2-pentyne, 3-methyl-1-butyne, 1-hexyne, 1-heptyne, 1-octyne, 1-nonyne, 1-decyne, and the like and combinations thereof. The presently preferred alkynes are acetylene and propyne.

The alkynes are primarily hydrogenated to the corresponding alkenes. For example, acetylene is primarily hydrogenated to ethylene; propyne is primarily hydrogenated to propylene; and the butynes are primarily hydrogenated to the corresponding butenes (e.g., 1-butene, 2-butenes).

Examples of suitable diolefins include those containing in the range of from 3 carbon atoms per molecule to about 12 carbon atoms per molecule. Such diolefins include, but are not limited to, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and the like and combinations thereof.

Presently preferred diolefins are propadiene, 1,2-butadiene, 1,3-butadiene, pentadienes (such as 1,3-pentadiene, 1,4-pentadiene, isoprene), cyclopentadienes (such as 1,3-cyclopentadiene) and dicyclopentadiene (also known as tricyclo[5.2.1]$^{2,6}$deca-3,8-diene). These diolefins are preferably hydrogenated to their corresponding monoolefins containing the same number of carbon atoms per molecule as the diolefins. For example, propadiene is hydrogenated to propylene, 1,2-butadiene and 1,3-butadiene are hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, and 1,3-cyclopentadiene is hydrogenated to cyclopentene.

Examples of suitable aromatic hydrocarbons include, but are not limited to, benzene, toluene, ethylbenzene, styrene, xylenes, and the like and combinations thereof.

Examples of suitable monoolefins include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohexenes, trimethylcyclohexenes, methylcyclooctenes, dimethylcyclooctenes, ethylcyclooctenes, and the like and combinations thereof.

Examples of suitable saturated hydrocarbons include, but are not limited to, methane, ethane, propane, butane, methylpropane, methylbutane, dimethylbutane, pentanes, hexanes, and the like and combinations thereof.

Furthermore, the hydrocarbon-containing fluid can contain in the range of from about 0.001 weight percent hydrogen to about 5 weight percent hydrogen, and up to 5000 parts per million by volume (ppmv) of carbon monoxide.

The hydrocarbon-containing fluid disclosed herein may contain an impurity at a level which does not significantly interfere with the hydrogenation process of a highly unsaturated hydrocarbon to a less unsaturated hydrocarbon as described herein. The term "impurity" as used herein denotes any component in a hydrocarbon-containing fluid that is not a major component. Examples of impurities other than an alkyne or a diolefin include, but are not limited to carbon monoxide, hydrogen sulfide, carbonyl sulfide (COS), carbon disulfide ($CS_2$), mercaptans (RSH), organic sulfides (RSR), organic disulfides (RSSR), thiophene, organic trisulfides, organic tetrasulfides, and the like and combinations thereof, wherein each R can be an alkyl or cycloalkyl or aryl group containing 1 carbon atom to about 15 carbon atoms, preferably 1 carbon atom to 10 carbon atoms. It is within the scope of this invention to have additional compounds (such as water, alcohols, ethers, aldehydes, ketones, carboxylic acids, esters, other oxygenated compounds, and the like and combinations thereof) present in the hydrocarbon-containing fluid, as long as they do not significantly interfere with the hydrogenation process of a highly unsaturated hydrocarbon to a less unsaturated hydrocarbon as described herein.

The hydrogenation process(es) of this invention is generally carried out by contacting a hydrocarbon-containing fluid comprising at least one highly unsaturated hydrocarbon, in the presence of hydrogen, with the catalyst composition of this invention under a hydrogenation condition. The hydrocarbon-containing fluid can be contacted by any suitable manner with the catalyst composition described herein which is contained within a hydrogenation zone. Such hydrogenation zone can comprise, for example, a reactor vessel.

The contacting step, of contacting the hydrocarbon-containing fluid with the catalyst composition disclosed herein, can be operated as a batch process step or, preferably, as a continuous process step. In the latter operation, a solid or fixed catalyst bed or a moving catalyst bed or a fluidized catalyst bed can be employed. Preferably, a fixed catalyst bed is employed. Any of these operational modes have advantages and disadvantages, and those skilled in the art can select the one most suitable for a particular hydrocarbon-containing fluid and catalyst composition.

The contacting step is preferably carried out within a hydrogenation zone, wherein is contained the catalyst composition disclosed herein, and under a hydrogenation condition that suitably promotes the hydrogenation process of a highly unsaturated hydrocarbon to a less unsaturated hydrocarbon as described herein. Such hydrogenation condition should be such as to avoid significant hydrogenation of a less unsaturated hydrocarbon(s) being initially present in the hydrocarbon-containing fluid to a saturated hydrocarbon(s) such as an alkane(s) or cycloalkane(s).

Generally, such hydrogenation process comprises the presence of hydrogen, preferably hydrogen gas, in an amount in the range of from about 0.1 mole of hydrogen employed for each mole of highly unsaturated hydrocarbon present in the hydrocarbon-containing fluid to about 1000 moles of hydrogen employed for each mole of highly unsaturated hydrocarbon present in the hydrocarbon-containing fluid. Preferably, such hydrogenation process comprises the presence of hydrogen, preferably hydrogen gas, in an amount in the range of from about 0.5 mole to about 500 moles of hydrogen employed for each mole of highly unsaturated hydrocarbon present in the hydrocarbon-containing fluid and, most preferably, in the range of from 0.7 mole to 200 moles of hydrogen employed for each mole of highly unsaturated hydrocarbon present in the hydrocarbon-containing fluid.

Generally, such hydrogenation condition comprises a temperature and a pressure necessary for the hydrogenation process(es) of this invention depending largely upon the activity of the catalyst composition, the hydrocarbon-containing fluid, and the desired extent of hydrogenation. Generally, such temperature is in the range of from about 10° C. to about 300° C., preferably in the range of from about 20° C. to about 250° C. and, most preferably, in the range of from 20° C. to 200° C. A suitable pressure is generally in the range of from about 15 pounds per square inch gauge (psig) to about 2000 psig, preferably in the range of from about 50 psig to about 1500 psig and, most preferably, in the range of from 100 psig to 1000 psig.

Such hydrogenation condition further comprises the flow rate at which the hydrocarbon-containing fluid is charged (i.e., the charge rate of hydrocarbon-containing fluid) to the hydrogenation zone. The flow rate is such as to provide a gas hourly space velocity ("GHSV") generally exceeding 1 liter/liter/hour. The term "gas hourly space velocity", as used herein, shall mean the numerical ratio of the rate at which a hydrocarbon-containing fluid is charged to the hydrogenation zone in liters per hour at standard condition of temperature and pressure ("STP") divided by the liters of catalyst composition contained in the hydrogenation zone to which the hydrocarbon-containing fluid is charged. Typically, the gas hourly space velocity of the hydrocarbon-containing fluid will be in the range of from about 1 to about 50,000 liters of hydrocarbon-containing fluid per liter of catalyst per hour (liter/liter/hour), preferably in the range of from about 750 to about 40,000 liter/liter/hour and, most preferably, in the range of from 1000 to about 30,000 liter/liter/hour.

If it is desired to regenerate the catalyst composition of this invention after prolonged use in the hydrogenation process(es) described herein, the regeneration can be accomplished by calcining the catalyst composition in an oxidizing atmosphere such as in air at a temperature that does not exceed about 700° C. to burn off carbonaceous and sulfur deposits. Optionally, the catalyst composition can be reimpregnated with palladium and a catalyst component comprising either silver or an alkali metal compound, or both silver and an alkali metal compound, and then dried and calcined as described herein for the production of a fresh catalyst composition of this invention.

The following examples are presented to further illustrate this invention and are not to be construed as unduly limiting the scope of this invention.

EXAMPLE I

This example illustrates the preparation of various palladium-containing catalyst compositions to be used in a hydrogenation process. It should be noted that differences in the weight percents of the various components, such as Pd, Ag, and KF, incorporated with the various inorganic support materials is in part due to the differences in pore volume and surface area of the respective inorganic support material. It should also be noted that it is generally known in the art that as the concentration of silver incorporated with the hydrogenation catalyst increases, the hydrogenation catalyst becomes less active. Similarly, it is also generally known in the art that as the concentration of an alkali metal, such as potassium, incorporated with the hydrogenation catalyst increases, the hydrogenation catalyst becomes less active.

Catalyst A (Control) was a commercially available Pd/Ag/alumina catalyst composition which contained about 0.018 weight percent palladium (Pd) and about 0.056 weight percent silver (Ag) on $\frac{7}{32}$ inch by $\frac{7}{32}$ inch $\alpha$-$Al_2O_3$ pellets. Control Catalyst A had a surface area measured by the BET method (Brunauer, Emmett and Teller method) employing $N_2$ of about 3 $m^2/g$ to about 5 $m^2/g$ and had been provided by United Catalyst Inc. (UCI), Louisville, Ky., under the product designation of "G83C". The G83C catalyst is a hydrogenation catalyst which is widely used in industry.

Catalyst B (Invention) was a Pd/Ag/$ZnAl_2O_4$ catalyst composition prepared as follows. A 150 gram quantity of commercially available gamma alumina (provided by Englehard Company, Elyria, Ohio, obtained as pre-calcined pellets having a diameter of about $\frac{1}{8}$ inch) was placed in a drying oven at 130° C. for about 1 hour. The thus-heated gamma alumina was then impregnated, by an incipient wetness impregnation technique (i.e., essentially completely filling the pores of the substrate material with a solution of the incorporating elements), with about 136 grams of zinc nitrate hexahydrate ($Zn(NO_3)_2.6H_2O$) which had been melted in a drying oven at a temperature of about 130° C. at a pressure of about atmospheric (i.e., about 14.7 psia) for about one hour. The impregnation of the gamma alumina pellets with the melted zinc nitrate hexahydrate was conducted by adding the melted zinc nitrate hexahydrate dropwise to the gamma alumina pellets over a 30 minute period using a 5 mL pipette. The gamma alumina pellets were continuously stirred during the addition of the melted zinc nitrate hexahydrate. When finished, the thus-zinc-incorporated alumina was placed in a drying oven at 130° C. for about 48 hours. The thus-dried zinc-incorporated alumina was then placed in a quartz calcining tube and slowly heated to 300° C. over a three-hour period under an air purge as $NO_x$ gas liberation was observed. The calcining tube was constantly purged with air during calcination. The temperature was maintained at 300° C. for 3 hours and then increased to 400° C. The 400° C. temperature was maintained overnight (approximately 16 hours) and then increased to 1100° C. over two hours and then maintained at 1100° C. for 7 hours. The furnace providing heat to the calcining tube was then turned off overnight (approximately 16 hours). The calcining tube was then heated to 1100° C. over 3 hours and then maintained at 1100° C. for 4 hours. The calcining tube was then allowed to cool for a time period of about 2 hours to thereby provide a zinc aluminate catalyst support. The zinc aluminate of the zinc aluminate catalyst support had a crystalline domain size of 1075 angstroms. The alpha alumina of the zinc aluminate catalyst support had a crystalline domain size of 465 angstroms. The "crystalline domain size" was determined from the line broadening of the X-ray diffraction profile. Analysis confirmed that the zinc aluminate catalyst support had a surface area of about 14 $m^2/g$, a pore volume of about 0.145 mL/g, and an average pore diameter of about 401 angstroms. In addition, the X-ray diffraction profile confirmed that the catalyst support had a zinc aluminate structure.

Then, a 0.037 gram quantity of palladium chloride ($PdCl_2$) was dissolved in 3 grams of distilled water with 20 drops of concentrated HCl to form a solution in a beaker. The solution was heated to almost dryness on a hot plate. A 30.11 gram quantity of distilled water was then added to reconstitute and prepare a $H_2PdCl_4$ solution.

A 100 gram quantity of the above-described zinc aluminate catalyst support was then impregnated with (i.e, soaked in) the above-described $H_2PdCl_4$ solution. The Pd-containing composition was then dried in air at 105° C. overnight (i.e., about 16 hours) to thereby provide a dried Pd-containing composition. The thus-dried Pd-containing composition was then calcined in air at 400° C. for about 16 hours to thereby provide a dried and calcined Pd-containing composition.

To aid in the removal of any chloride(s), the dried and calcined Pd-containing composition was added to a 500 mL quantity of distilled water and heated to boiling. The solution was decanted off. This boiling and decanting procedure was repeated three times. The remaining Pd-containing composition was then rinsed for about 5 minutes with distilled water. The remaining Pd-containing composition was then dried in air at 105° C. overnight (i.e., about 16 hours) to thereby provide a dried Pd-containing composition. The thus-dried Pd-containing composition was then impregnated with (i.e., soaked in) a solution of 0.328 grams of silver nitrate ($AgNO_3$) in 75 grams of distilled water for about 120 minutes. The solution was decanted off. The remaining palladium-and-silver-containing composition was then dried in air at 105° C. for about 3 hours and then calcined in air at 400° C. for about 5.5 hours to thereby provide Invention Catalyst B (a Pd/Ag/ZnAl$_2$O$_4$ catalyst composition). Invention Catalyst B contained 0.018 weight percent Pd and 0.128 weight percent Ag.

Catalyst C (Control) was a Pd/Ag/KF/alumina catalyst composition prepared as follows. A 1000 mL potassium fluoride (KF) solution containing a 29.27 gram quantity of potassium fluoride (KF) dissolved in distilled water was prepared. To 400 mL of such 1000 mL KF solution was added a 100.44 gram quantity of the above-described G83C (Control Catalyst A) to thereby provide a KF/G83C-containing solution. The KF/G83C-containing solution was heated to boiling. The solution was decanted off and the remaining solid was rinsed twice with distilled water. Each rinsing lasted about 5 minutes. The procedure was then repeated using another 400 mL of such 1000 mL KF solution. The procedure was then repeated using the remaining 200 mL of such 1000 mL KF solution. The remaining KF/G83C composition was then dried in air at 105° C. overnight (i.e., about 16 hours) to thereby provide a dried KF/G83C composition. The thus-dried KF/G83C composition was then calcined in air at 400° C. for about 2 hours to thereby provide a dried and calcined KF/G83C composition. A 66.03 gram quantity of such dried and calcined KF/G83C composition was then impregnated, using an incipient wetness technique (i.e., essentially completely filling the pores of a substrate material with a solution of the incorporating elements) with a KF solution of 0.50 gram KF dissolved in 22.10 grams of distilled water. The resulting KF/G83C composition was then dried in air at 105° C. for about 5 hours to thereby provide a dried KF/G83C composition. The thus-dried KF/G83C composition was then calcined in air at 526° C. overnight (i.e., about 16 hours) to thereby provide Control Catalyst C. Control Catalyst C contained 0.018 weight percent Pd, 0.056 weight percent Ag, and 0.52 weight percent K.

Catalyst D (Invention) was a Pd/Ag/KF/ZnAl$_2$O$_4$ catalyst composition prepared as follows. A 1000 mL potassium fluoride (KF) solution containing a 29.0 gram quantity of potassium fluoride (KF) dissolved in distilled water was prepared. To 400 mL of such 1000 mL KF solution was added a 70.95 gram quantity of the above-described Invention Catalyst B (a Pd/Ag/ZnAl$_2$O$_4$ catalyst composition) to thereby provide a KF/Pd/Ag/ZnAl$_2$O$_4$-containing solution. The KF/Pd/Ag/ZnAl$_2$O$_4$-containing solution was heated to boiling. The solution was decanted off and the remaining solid was rinsed twice with distilled water. Each rinsing lasted about 5 minutes. The procedure was then repeated using another 400 mL of such 1000 mL KF solution. The procedure was then repeated using the remaining 200 mL of such 1000 mL KF solution. The resulting Pd/Ag/KF/ZnAl$_2$O$_4$ composition was then rinsed five more times with distilled water. Each rinsing lasted about 5 minutes. The resulting Pd/Ag/KF/ZnAl$_2$O$_4$ composition was then dried in air at 105° C. overnight (i.e., about 16 hours) to thereby provide a dried Pd/Ag/KF/ZnAl$_2$O$_4$ composition. A 66.0 gram quantity of such dried Pd/Ag/KF/ZnAl$_2$O$_4$ composition was then impregnated, using an incipient wetness technique (i.e., essentially completely filling the pores of a substrate material with a solution of the incorporating elements) with a KF solution of 0.49 gram KF dissolved in 22.0 grams of distilled water. The remaining Pd/Ag/KF/ZnAl$_2$O$_4$ composition was then dried in air at 105° C. for about 3 hours to thereby provide a dried Pd/Ag/KF/ZnAl$_2$O$_4$ composition. The thus-dried Pd/Ag/KF/ZnAl$_2$O$_4$ composition was then calcined in air at 526° C. overnight (i.e., about 16 hours) to thereby provide Invention Catalyst D. Invention Catalyst D contained 0.018 weight percent Pd, 0.128 weight percent Ag, and 0.68 weight percent K.

EXAMPLE II

This example illustrates the performance of the catalyst compositions described herein in Example I in a hydrogenation process.

About 23 grams (i.e., about 20 milliliters) of each of the above described Example I catalysts were packed into a water jacketed stainless steel reactor (0.5 inch inner diameter; 18 inches long). Thermocouples were inserted into a thermal well which ran through the center and coaxial with the reactor which was heated with an external water bath. The catalyst was then treated with hydrogen gas flowing at about 50 psig to about 200 psig (about 100 cc/min to about 200 cc/min) at a temperature of about 25° C. to about 60° C. for about 1 hour to about 16 hours. Thereafter a hydrocarbon-containing fluid, typical of a feed from the overhead of a front-end deethanizer of an ethylene plant, was continuously introduced into the reactor at a pressure of 200 psig, at a temperature of about 38° C., and at a feed rate of about 900 cc/minute. The hydrocarbon-containing fluid contained approximately 19.9 mole percent hydrogen; 10.3 mole percent ethane; 38.8 mole percent ethylene; 0.38 mole percent acetylene; 0.02 mole percent carbon monoxide (CO); 30.5 mole percent methane; trace amounts (i.e., less than 0.007 mole percent of each) of propane and propylene; and essentially no others.

The reactor was then "lined out" at different temperatures with the catalyst always having hydrocarbon-containing fluid passing over for at least 6 minutes. The reactor effluent, i.e., the product stream, was then analyzed by gas chromatography.

In the results shown below in Table I, T1 is referred to as the "cleanup" temperature which is the temperature at which the acetylene concentration falls below 20 ppm (20 parts acetylene per million parts hydrocarbon-containing fluid by weight). In a hydrogenation process, a low T1 is desirable. A low T1 indicates a higher activity and a longer run life of the catalyst. As the catalyst is used in a hydrogenation process, operating temperatures must be steadily increased over time to compensate for the decrease in activity of the catalyst. However, there is an upper temperature limit (T2) above which the uncontrollable hydrogenation of ethylene to ethane will occur. Thus, a low T1 allows an overall longer run life of the catalyst. In Table I, T2 is referred to as the "runaway" temperature which is the temperature at which 2 mole % of ethylene produced is hydrogenated to ethane (i.e., an exothermic "runaway" reaction is occurring). In Table I, ΔT is the difference between T2 and T1. The ΔT is a measure of ethylene selectivity which can also be viewed as a window of operability of the reaction. The greater the temperature difference between T2 and T1 (i.e., the greater the ΔT) attained with a particular catalyst, the more satisfactorily will this catalyst perform as a hydrogenation catalyst composition.

In addition, in Table I "hydrocarbon make at T1" refers to the amount of a particular hydrocarbon being made or produced at T1. For example, any hydrocarbon containing 4 carbon atoms is referred to as "C$_4$" thus, "C$_4$ make at T1" refers to the amount (in parts by weight C$_4$ per million parts by weight hydrocarbon-containing fluid, i.e., ppm C$_4$) of C$_4$ being made or produced at T1. Any hydrocarbons containing 6 or more carbon atoms per molecule is referred to as "heavies" thus, "heavies make at T1" refers to the amount, in ppm, of any hydrocarbons containing 6 or more carbon atoms being made or produced at T1.

TABLE I

| Catalyst | Temperatures | | | Hydrocarbon Make at T1[a] | |
|---|---|---|---|---|---|
| | T1 | T2 | ΔT | $C_4$[b] | Heavies[c] |
| Catalyst A (Control)[e] | 128 | 162 | 34 | 630 | 340 |
| Catalyst B (Invention)[f] | 109 | 138 | 29 | 640 | 320 |
| Catalyst C (Control)[g] | 163 | 265[d] | 100 | 520 | 270 |
| Catalyst D (Invention)[h] | 125 | 190 | 65 | 580 | 390 |

[a]The values shown are in parts per million by weight (ppm)
[b]$C_4$ denotes hydrocarbons containing 4 carbon atoms such as butanes, butenes, and butadienes in ppm
[c]Heavies denotes hydrocarbons containing 6 or more carbon atoms in ppm
[d]Temperature was estimated by extrapolation because the temperature was not achievable with the equipment used in Example II.
[e]Catalyst A: 0.018 wt % Pd /0.056 wt % Ag / alumina
[f]Catalyst B: 0.018 wt % Pd / 0.128 wt % Ag / $ZnAl_2O_4$
[g]Catalyst C: 0.018 wt % Pd / 0.056 wt % Ag / 0.52 wt % potassium (K) / alumina
[h]Catalyst D: 0.018 wt % Pd / 0.128 wt % Ag / 0.68 wt % K / $ZnAl_2O_4$ Test data in Table I clearly show that the Invention Catalysts, which all contained an inorganic support material comprising a zinc aluminate prepared by the inventive process(es) disclosed herein, performed better than the Control Catalysts, which contained an inorganic support material of alumina, in several key areas of hydrogenation such as T1, ΔT, and hydrocarbon make at T1.

Concerning T1, Invention Catalyst B (Pd/Ag/$ZnAl_2O_4$) exhibited a significantly lower T1 than Control Catalyst A (Pd/Ag/alumina) which is quite unexpected when considering that Invention Catalyst B contained almost twice as much silver as Control Catalyst A. Invention Catalyst D (Pd/Ag/KF/$ZnAl_2O_4$) exhibited a significantly lower T1 than Control Catalyst C (Pd/Ag/KF/alumina) which is also quite unexpected when considering that Invention Catalyst D contained almost twice as much silver and about 0.10 weight percent more potassium (K) compared to Control Catalyst C. The T1 data demonstrate that the Invention Catalysts exhibited a lower T1 than the Control Catalysts, even with increased silver and K loadings, which allows a lower temperature to be used to begin "cleanup" of the acetylene which translates into lower operating costs.

Concerning ΔT, the Invention Catalysts exhibited similar ΔTs compared to the Control Catalysts even with increased silver and K loadings. Invention Catalyst B exhibited a ΔT comparable to Control Catalyst A and a significantly lower T1 of only 109° C. even though Invention Catalyst B contained twice as much silver as Control Catalyst A. Similarly, Invention Catalyst D exhibited a ΔT comparable to Control Catalyst C with a T1 significantly less than Control Catalyst C even though Invention Catalyst D contained almost twice as much silver and about 0.10 weight percent more K. The T1 and ΔT data demonstrate that the Invention Catalysts were able to exhibit a large ΔT in which the hydrogenation reaction can be conducted while maintaining a low T1.

Concerning hydrocarbon make at T1, the data demonstrate that the Invention Catalysts exhibited hydrocarbon make at T1 in amounts similar to, if not better than, the Control Catalysts even though the Invention Catalysts contained increased silver and K loadings.

The performance of the Invention Catalysts, as compared to the Control Catalysts, is superior when comparing several key areas of hydrogenation such as T1, ΔT, and hydrocarbon make at T1. The improvement in catalyst performance is believed to be due to the novel process(es) of using a novel catalyst composition comprising palladium, an inorganic support material comprising a zinc aluminate, and a catalyst component comprising silver or an alkali metal compound, or both silver and an alkali metal compound prepared according to the inventive process(es) disclosed herein.

EXAMPLE III

This example illustrates the preparation of various palladium-containing catalysts to be used in a hydrogenation process.

Catalyst E (Control) was a Pd/Ag/KF/alumina catalyst composition prepared as follows. A 500 gram quantity of commercially available alpha alumina (provided by Condea Vista Company, Houston, Tex., obtained as pre-calcined tablets having a diameter of about 3.1 mm, a length of about 3.1 mm, and a surface area of about 9 $m^2$/g under the product designation "CATAPAL") was placed in a drying oven at 120° C. for about 30 minutes. Then, a 0.5 gram quantity of palladium chloride ($PdCl_2$) was dissolved in 25 grams of distilled water with 10 drops of concentrated HCl to form a solution in a beaker. The solution was heated to almost dryness on a hot plate. A quantity of distilled water was then added to reconstitute to 60 grams and prepare a $H_2PdCl_4$ solution containing 0.5 weight percent palladium.

A 50 gram quantity of the above-described alumina support was then impregnated with (i.e, soaked in) 2 grams of the above-described $H_2PdCl_4$ solution, diluted with 25 grams of distilled water, for about 1 hour. The solution was decanted off. The remaining Pd-containing composition was then dried in air at 125° C. for 1 hour to thereby provide a dried Pd-containing composition. The thus-dried Pd-containing composition was then calcined in air at 538° C. for about 3 hours to thereby provide a dried and calcined Pd-containing composition.

The thus-dried and calcined Pd-containing composition was then impregnated with (i.e., soaked in) a solution of 0.095 gram of silver nitrate ($AgNO_3$) in 50 grams of distilled water for about 30 minutes. The solution was decanted off. The remaining palladium-and-silver-containing composition was then dried in air at 125° C. for about 1 hour and then calcined in air at 538° C. for about 3 hours to thereby provide a Pd/Ag/alumina composition containing 0.02 weight percent Pd and 0.06 weight percent Ag.

A 25 gram quantity of such dried and calcined Pd/Ag/alumina composition was then impregnated, using an incipient wetness technique (i.e., essentially completely filling the pores of a substrate material with a solution of the incorporating elements) with a KF solution of 0.11 gram KF dissolved in 6.0 grams of distilled water.

The remaining Pd/Ag/KF/alumina composition was then dried in air at 125° C. for about 1 hour to thereby provide a dried Pd/Ag/KF/alumina composition. The thus-dried Pd/Ag/KF/alumina composition was then calcined in air at 538° C. for 3 hours to thereby provide Control Catalyst E. Control Catalyst E contained 0.02 weight percent Pd, 0.06 weight percent Ag, and 0.3 weight percent potassium (K).

Catalyst F (Control) was a Pd/Ag/KF/alumina catalyst composition prepared in the same manner as the above-described Control Catalyst E with the following exceptions. A 50 gram quantity of commercially available alpha alumina (provided by United Catalysts Inc. (UCI), Louisville, Ky., obtained as pre-calcined tablets having a diameter of about 3.8 mm, a length of 4 mm, and a surface area of about 4 $m^2$/g) was used in lieu of the Condea Vista Company CATAPAL alumina. Also, the thus-dried and calcined Pd-containing composition was impregnated with a solution of 0.0465 gram of silver nitrate ($AgNO_3$) in 11.5 grams of distilled water using an incipient wetness technique (i.e., essentially completely filling the pores of the substrate material with a solution of the incorporating elements) instead of soaking the composition in the silver nitrate solution described herein for Control Catalyst E.

Control Catalyst F contained 0.02 weight percent Pd, 0.06 weight percent Ag, and 0.3 weight percent K.

Catalyst G (Invention) was a $Pd/Ag/KF/ZnAl_2O_4$ catalyst composition prepared as follows. A 170 gram quantity of commercially available gamma alumina (provided by UOP Inc., McCook, Ill., obtained as pre-calcined extrudates having a diameter of about ⅛ inch under the product designation "EAB-3") was placed in a drying oven at 120° C. for about 1 hour. The thus-heated gamma alumina was then impregnated with about 163 grams of zinc nitrate hexahydrate ($Zn(NO_3)_2 \cdot 6H_2O$) which had been melted in a drying oven at a temperature of about 120° C. at a pressure of about atmospheric (i.e., about 14.7 psia) for about one hour. The impregnation of the gamma alumina pellets with the melted zinc nitrate hexahydrate was conducted by adding the melted zinc nitrate hexahydrate dropwise to the gamma alumina pellets over a 30 minute period using a 5 mL pipette. The gamma alumina extrudates were continuously stirred during the addition of the melted zinc nitrate hexahydrate. When finished, the thus-zinc-incorporated alumina was placed in a drying oven at 120° C. for about 1 hour. The thus-dried zinc-incorporated alumina was then placed in a quartz calcining tube and the temperature was slowly increased to 310° C. over a six-hour period under an air purge as $NO_x$ gas liberation was observed. The calcining tube was constantly purged with air during calcination. The temperature was maintained at 310° C. for 15 hours and then increased to 400° C. The 400° C. temperature was maintained for 3 hours and then increased to 1100° C. over two hours and then maintained at 1100° C. for 11 hours. The furnace providing heat to the calcining tube was then turned off overnight (approximately 16 hours) to thereby provide a zinc aluminate catalyst support. The zinc aluminate of the zinc aluminate catalyst support had a crystalline domain size of 330 angstroms. The alpha alumina of the zinc aluminate catalyst support had a crystalline domain size of 510 angstroms. The "crystalline domain size" was determined from the line broadening of the X-ray diffraction profile. Analysis confirmed that the zinc aluminate catalyst support had a surface area of about 14 $m^2/g$, a pore volume of about 0.112 mL/g, and an average pore diameter of about 321 angstroms. In addition, the X-ray diffraction profile confirmed that the catalyst support had a zinc aluminate structure.

A 50 gram quantity of the above-described zinc aluminate catalyst support was then impregnated with (i.e, soaked in) 10 grams of a 0.1 percent palladium (as $H_2PdCl_4$) solution diluted to 30 grams with distilled water for about 1 hour. The solution was decanted off. The remaining Pd-containing composition was then dried in air at 125° C. overnight for 1 hour to thereby provide a dried Pd-containing composition.

The thus-dried Pd-containing composition was then calcined in air at 538° C. for about 3 hours to thereby provide a dried and calcined Pd-containing composition.

The thus-dried and calcined Pd-containing composition was then impregnated with (i.e., soaked in) a solution of 0.095 gram of silver nitrate (AgNO3) in 50 grams of distilled water for about 30 minutes. The solution was decanted off. The remaining palladium-and-silver-containing composition was then dried in air at 125° C. for about 1 hour and then calcined in air at 538° C. for about 3 hours to thereby provide a $Pd/Ag/ZnAl_2O_4$ catalyst composition containing 0.02 weight percent Pd and 0.06 weight percent Ag.

A 25.1 gram quantity of such dried and calcined Pd/Ag/$ZnAl_2O_4$ composition was then impregnated, using an incipient wetness technique (i.e., essentially completely filling the pores of a substrate material with a solution of the incorporating elements) with a KF solution of 0.11 gram KF dissolved in 4.2 grams of distilled water.

The remaining $Pd/Ag/KF/ZnAl_2O_4$ composition was then dried in air at 125° C. for about 1 hour to thereby provide a dried $Pd/Ag/KF/ZnAl_2O_4$ composition. The thus-dried $Pd/Ag/KF/ZnAl_2O_4$ composition was then calcined in air at 538° C. for 3 hours to thereby provide Invention Catalyst G. Invention Catalyst G contained 0.02 weight percent Pd, 0.06 weight percent Ag, and 0.3 weight percent K.

Catalyst H (Invention) was a $Pd/Ag/KF/ZnAl_2O_4$ catalyst composition prepared in the same manner as the above-described Invention Catalyst G with the following exceptions. The zinc aluminate catalyst support was prepared in the following manner.

A 500 gram quantity of commercially available gamma alumina (provided by Englehard company, Elyria, Ohio, obtained as pre-calcined extrudates having a diameter of about 1/12 inch) was placed in a drying oven at 120° C. for about 30 minutes. The thus-heated gamma alumina was then impregnated with about 452 grams of zinc nitrate hexahydrate ($Zn(NO_3)_2 \cdot 6H_2O$) which had been melted in a drying oven at a temperature of about 120° C. at a pressure of about atmospheric (i.e., about 14.7 psia) for about 1 hour. The impregnation of the gamma alumina extrudates with the melted zinc nitrate was conducted by adding the melted zinc nitrate hexahydrate dropwise to the gamma alumina extrudates over a 30 minute period using a 5 mL pipette. The gamma alumina tablets were continuously stirred during the addition of the melted zinc nitrate hexahydrate.

When finished, the thus-zinc-incorporated alumina was placed in a drying oven at 120° C. overnight (approximately 16 hours). The thus-dried zinc-incorporated alumina was then placed in a quartz calcining tube and the temperature was slowly increased to 250° C. and maintained at 250° C. for 16 hours under an air purge. The temperature was then increased to 350° C. and maintained at 350° C. for 3 hours. The temperature was then increased to 450° C. and maintained at 450° C. for 3 hours. The temperature was then increased to 550° C. and maintained at 550° C. for 2 hours. During such heating $NO_x$ gas liberation was observed.

The calcining tube was then allowed to cool overnight (approximately 16 hours). The zinc-incorporated alumina was then transferred to a porcelain crucible and the temperature was then increased under a Programmed Temperature Ramp procedure as follows. The temperature was increased to 500° C. over a time period of about 4 hours and then maintained at 500° C. for about 0.5 hour. The temperature was then increased to 800° C. over a time period of about 2.5 hours and then maintained at 800° C. for a time period of about 4.5 hours. The temperature was then increased to 1130° C. over a time period of about 2.75 hours and then maintained at 1130° C. for a time period of about 10 hours. The porcelain crucible was then allowed to cool for a time period of about 2 hours to thereby provide a zinc aluminate catalyst support.

The temperatures recited for the Programmed Temperature Ramp were the temperatures of the program. The actual temperatures achieved were slightly less than the programmed temperatures as follows:

500° C. programmed=494° C. actual; 800° C. programmed= 779° C. actual; and 1130° C. programmed=1108° C. actual.

The zinc aluminate of the zinc aluminate catalyst support had a crystalline domain size of 270 angstroms. The alpha alumina of the zinc aluminate catalyst support had a crystalline domain size of 330 angstroms. The "crystalline domain size" was determined from the line broadening of the X-ray diffraction profile. Analysis confirmed that the zinc aluminate catalyst support had a surface area of about 14 m²/g, a pore volume of about 0.125 mL/g, and an average pore diameter of about 354 angstroms. In addition, the X-ray diffraction profile confirmed that the catalyst support had a zinc aluminate structure.

Other exceptions to the manner of preparation as described herein for Invention Catalyst G are as follows. A 0.5 percent palladium (as $H_2PdCl_4$) solution was used in lieu of the 0.1 percent palladium (as $H_2PdCl_4$) solution described herein for Invention Catalyst G.

Catalyst H contained 0.023 weight percent Pd, 0.115 weight percent Ag, and 0.5 weight percent K.

Catalyst I (Invention) was a Pd/Ag/KF/$ZnAl_2O_4$ catalyst composition which was prepared in the same manner as the above-described Invention Catalyst H. Invention Catalyst I contained 0.026 weight percent Pd, 0.130 weight percent Ag, and 0.5 weight percent K.

Catalyst J (Invention) was a Pd/Ag/KF/$MgAl_2O_4$ catalyst composition which was prepared in the same manner as the above-described Invention Catalyst G with the following exception. A magnesium aluminate support was used in lieu of the zinc aluminate support described herein for Invention Catalyst G. The magnesium aluminate support was prepared as follows. A 110.4 gram quantity of commercially available gamma alumina (provided by UOP, Inc., McCook, Ill. obtained as pre-calcined extrudates having a diameter of about ⅛ inch) was placed in a drying oven at 120° C. for about 30 minutes. The thus-heated gamma alumina was then impregnated with about 72.2 grams of magnesium nitrate hexahydrate ($Mg(NO_3)_2.6H_2O$) which had been melted in a drying oven at a temperature of about 120° C. at a pressure of about atmospheric (i.e., about 14.7 psia) for about 30 minutes. The impregnation of the gamma alumina extrudates with the melted magnesium nitrate was conducted by adding the melted magnesium nitrate hexahydrate dropwise to the gamma alumina extrudates over a 30 minute period using a 5 mL pipette. The gamma alumina extrudates were continuously stirred during the addition of the melted magnesium nitrate hexahydrate. The melted magnesium nitrate hexahydrate impregnating solution began to solidify during the addition of such magnesium nitrate hexahydrate to the gamma alumina tablets resulting in the melted magnesium nitrate solution having to be returned to the drying oven to be reheated at 120° C. for a period of about 3 minutes approximately every 10 minutes throughout the 30-minute period of impregnating the gamma alumina extrudates.

When finished, the thus-magnesium-incorporated alumina was placed in a drying oven at 120° C. for about 48 hours. The thus-dried magnesium-incorporated alumina was then placed in a quartz calcining tube and the temperature was slowly increased to 130° C. and maintained at 130° C. for a 2 hour period under an air purge. The temperature was then increased to 250° C. and maintained at 250° C. for 2 hours. The temperature was then increased to 350° C. and maintained at 350° C. for 2 hours. The temperature was then increased to 400° C. and maintained at 400° C. for 16 hours. The temperature was then increased to 500° C. and maintained at 500° C. for 3 hours. The temperature was then increased to 600° C. and maintained at 600° C. for 2 hours. The temperature was then increased to 650° C. and maintained at 650° C. for 2 hours. During such heating, $NO_x$ gas liberation was observed.

The magnesium-incorporated alumina was then transferred to a porcelain crucible and the temperature was then increased under the same Programmed Temperature Ramp procedure as described herein for Invention Catalyst H. The porcelain crucible was then allowed to cool for a time period of about 2 hours to thereby provide a magnesium aluminate catalyst support.

Invention Catalyst J contained 0.02 weight percent Pd, 0.06 weight percent Ag, and 0.3 weight percent K.

Catalyst K (Invention) was a Pd/Ag/KF/$CaAl_2O_4$ catalyst composition which was prepared in the same manner as the above-described Invention Catalyst G with the following exception. A calcium aluminate support was used in lieu of the zinc aluminate support described herein for Invention Catalyst G. The calcium aluminate support was prepared in the following manner.

A 100 gram quantity of commercially available gamma alumina (provided by UOP Inc., McCook, Ill., obtained as pre-calcined tablets having a diameter of about ⅛ inch) was placed in a drying oven at a temperature of about 120° C. for a period of about 15 minutes. The thus-heated gamma alumina was then impregnated with about 60 grams of calcium nitrate tetrahydrate ($Ca(NO_3)_2.4H_2O$) which, after the addition of 20 grams of deionized water, had been melted in a drying oven at a temperature of about 120° C. at a pressure of about atmospheric (i.e., about 14.7 psia) for about 15 minutes. The impregnation of the gamma alumina tablets with the melted calcium nitrate tetrahydrate was conducted by adding the melted calcium nitrate tetrahydrate dropwise to the gamma alumina tablets over a 30 minute period using a 5 mL pipette. The gamma alumina tablets were continuously stirred during the addition of the melted calcium nitrate tetrahydrate. When finished, the thus-calcium-incorporated alumina was placed in a drying oven and heated at 120° C. for 3 hours.

The thus-dried calcium incorporated alumina was then placed in a quartz calcining tube and heated to 120° C. for 3 hours. The temperature was then increased to 220° C. and maintained at 220° C. for a period of 3 hours. The temperature was then increased to 330° C. and maintained at 330° C. for a period of 15 hours. The temperature was then increased to 400° C. and maintained at 400° C. for a period of 3 hours. The temperature was then increased to 500° C. and maintained at 500° C. for a period of 2 hours. The temperature was then increased to 600° C. and maintained at 600° C. for a period of 1 hour. The liberation of $NO_x$ gas was not observed at 600° C. The calcining tube was then allowed to cool to room temperature (i.e., about 20° C. to about 25° C.). The calcium-incorporated alumina was then transferred to a porcelain crucible and the temperature was then increased under the same Programmed Temperature Ramp as recited herein for Invention Catalyst H. After such Programmed Temperature Ramp heating, the porcelain crucible was then allowed to cool for a time period of about 2 hours to thereby provide a calcium aluminate catalyst support. The calcium aluminate of the calcium aluminate catalyst support had a crystalline domain size of 405 angstroms. The alpha alumina of the calcium aluminate catalyst support had a crystalline domain size of 535 angstroms. The "crystalline domain size" was determined from the line broadening of the X-ray diffraction profile. Analysis confirmed that the calcium aluminate catalyst support had a surface area of about 11 m²/g, a pore volume of about 0.129 mL/g, and an average pore diameter of about 468 angstroms. In addition, the X-ray diffraction profile confirmed that the catalyst support had a calcium aluminate structure.

Invention Catalyst K contained 0.02 weight percent Pd, 0.06 weight percent Ag, and 0.3 weight percent K.

EXAMPLE IV

This example illustrates the performance of the catalyst compositions, described herein in Example III, in a hydrogenation process. The hydrogenation process of Example IV was conducted in the same manner as the process described herein in Example II with the following exceptions.

The catalysts described herein under Example III were used in lieu of the catalysts of Example I.

A lab-prepared hydrocarbon-containing fluid was used in lieu of the hydrocarbon-containing fluid described herein for Example II. The hydrocarbon-containing fluid used in Example IV contained approximately 29.0 mole percent hydrogen; 0.007 mole percent ethane; 41.5 mole percent ethylene; 0.20 mole percent acetylene; 0.025 mole percent CO; 29.3 mole percent methane; and essentially no others.

In the results shown below in Table II, T1, T2, ΔT, and "hydrocarbon make at T1" represent the same type of information as described herein under Example II, but the data are from the runs of Example IV. In addition, ethane is referred to as "$C_2$" thus, "$C_2$ make at T1" refers to the amount (in parts by weight ethane per million parts by weight hydrocarbon-containing fluid, i.e., ppm ethane) of ethane being made or produced at T1.

TABLE II

| | Temperatures | | | Hydrocarbon Make at T1[a] | | |
|---|---|---|---|---|---|---|
| Catalyst | T1 | T2 | ΔT | $C_2$[b] | $C_4$[c] | Heavies[d] |
| Catalyst E (Control)[e] | 110 | 192 | 82 | 600 | 400 | 60 |
| Catalyst F (Control)[f] | 121 | 210 | 89 | 960 | 440 | 100 |
| Catalyst G (Invention)[g] | 112 | 194 | 82 | 900 | 380 | 50 |
| Catalyst H (Invention)[h] | 104 | 192 | 88 | 248 | 310 | 45 |
| Catalyst I (Invention)[i] | 99 | 182 | 83 | 380 | 336 | 51 |
| Catalyst J (Invention)[j] | 103 | 159 | 56 | 1430 | 370 | 70 |
| Catalyst K (Invention)[k] | 123 | 192 | 69 | 880 | 386 | 62 |

[a]The values shown are in parts per million by weight (ppm)
[b]$C_2$ denotes ethane in ppm
[c]$C_4$ denotes hydrocarbons containing 4 carbon atoms such as butanes, butenes, and butadienes in ppm
[d]Heavies denotes hydrocarbons containing 6 or more carbon atoms in ppm
[e]Catalyst E: 0.02 wt % Pd / 0.06 wt % Ag / 0.3 wt % potassium (K) / alumina
[f]Catalyst F: 0.02 wt % Pd / 0.06 wt % Ag / 0.3 wt % K / alumina
[g]Catalyst G: 0.02 wt % Pd / 0.06 wt % Ag / 0.3 wt % K / $ZnAl_2O_4$
[h]Catalyst H: 0.023 wt % Pd / 0.115 wt % Ag / 0.5 wt % K / $ZnAl_2O_4$
[i]Catalyst I: 0.026 wt % Pd / 0.130 wt % Ag / 0.5 wt % K / $ZnAl_2O_4$
[j]Catalyst J: 0.02 wt % Pd / 0.06 wt % Ag / 0.3 wt % K / $MgAl_2O_4$
[k]Catalyst K: 0.02 wt % Pd / 0.06 wt % Ag / 0.3 wt % K / $CaAl_2O_4$ Test data in Table II clearly show that the Invention Catalysts, which contained palladium, a catalyst component comprising silver and an alkali metal compound, and an inorganic support material comprising a zinc aluminate, a magnesium aluminate, or a calcium aluminate prepared according to the inventive process(es) disclosed herein, performed better than the Control Catalysts in several key areas of hydrogenation such as T1, ΔT, and hydrocarbon make at T1.

Concerning T1, the Invention Catalysts exhibited significantly lower T1s when compared to the Control Catalysts even with increased loadings of silver and potassium (such as Invention Catalysts H and I). Astonishingly, Invention Catalyst I exhibited a T1 of only 99° C. The T1 data demonstrate that the Invention Catalysts exhibited comparable, if not lower, T1s than the Control Catalysts which allows a lower temperature to be used to begin "cleanup" of the acetylene which translates into lower operating costs.

Concerning ΔT, the Invention Catalysts exhibited similar ΔTs compared to the Control Catalysts even with increased loadings of silver and potassium (such as Invention Catalysts H and I). Invention Catalysts H and I exhibited astonishingly low T1s while maintaining ΔTs comparable to the Control Catalysts. The T1 and ΔT data demonstrate that the Invention Catalysts were able to exhibit a large ΔT in which the hydrogenation reaction can be conducted while maintaining a low T1.

Concerning hydrocarbon make at T1, the data demonstrate that the Invention Catalysts exhibited low hydrocarbon make at T1 when compared to the Control Catalysts. Such data is significant especially when combined with the data demonstrating ΔTs comparable to the Control Catalysts and significantly lower T1s.

The performance of the Invention Catalysts, as compared to the Control Catalysts, is superior when comparing several key areas of hydrogenation such as T1, ΔT, and hydrocarbon on make at T1. The improvement in catalyst performance is believed to be due to the novel process of using a novel catalyst composition comprising palladium, a catalyst component comprising silver and/or an alkali metal compound, and an inorganic support material comprising a zinc aluminate, a magnesium aluminate, or a calcium aluminate prepared according to the inventive process(es) disclosed herein.

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

What is claimed is:

1. A process of making a catalyst composition comprising impregnating a metal aluminate catalyst support with palladium and a catalyst component selected from the group consisting of silver and an alkali metal compound wherein said metal aluminate catalyst support is prepared by a process comprising:

(a) incorporating alumina with a melted metal component to thereby provide a metal-incorporated alumina, and (b) calcining said metal-incorporated alumina under a calcining condition to thereby provide said metal aluminate catalyst support wherein said calcining condition comprises a temperature in the range of from about 1100° C. to about 1350° C., a pressure in the range of from about 7 pounds per square inch absolute (psia) to about 750 psia, and a time period in the range of from about 1 hour to about 60 hours; and further wherein said melted metal component comprises a metal component having been melted under a melting condition.

2. A process according to claim 1 wherein said incorporating step (a) comprises impregnating said alumina with said melted metal component.

3. A process according to claim 2 wherein said melting condition comprises:

a temperature below the decomposition temperature of said metal component, a time period in the range of from about 1 minute to about 2 hours, and a pressure in the range of from about atmospheric to about 150 psia.

4. A process according to claim 3 wherein said impregnating comprises adding said melted metal component to said alumina by pouring said melted metal component onto the surface of said alumina to thereby provide a metal-incorporated alumina having substantially all the surface area of said alumina coated with said melted metal component.

5. A process according to claim 4 wherein said melted metal component is poured over the surface of said alumina while said alumina is under constant stirring or tumbling.

6. A process according to claim 5 wherein said metal component is selected from the group consisting of a zinc component, a magnesium component, a calcium component, a barium component, a beryllium component, a cobalt component, an iron component, a manganese component, a strontium component, a lithium component, a potassium component, and combinations thereof.

7. A process according to claim 6 wherein said metal component is selected from the group consisting of a zinc component, a magnesium component, a calcium component, and combinations thereof.

8. A process according to claim 1 wherein the amount of said metal component incorporated with said alumina provides for said metal aluminate catalyst support having an amount of metal aluminate generally in the range of from about 1 weight percent of the total weight of said metal aluminate catalyst support to about 100 weight percent.

9. A process according to claim 1 wherein said metal component is selected from the group consisting of a zinc component, a magnesium component, a calcium component, a barium component, a beryllium component, a cobalt component, an iron component, a manganese component, a strontium component, a lithium component, a potassium component, and combinations thereof.

10. A process according to claim 9 wherein said zinc component is selected from the group consisting of zinc nitrate hexahydrate, zinc nitrate, hydrated zinc nitrate, zinc chloride, zinc acetate dihydrate, zinc acetylacetonate hydrate, zinc carbonate hydroxide monohydrate, zinc perchlorate hexahydrate, hydrated zinc sulfate, zinc sulfate monohydrate, zinc sulfate heptahydrate, and combinations thereof.

11. A process according to claim 9 wherein said magnesium component is selected from the group consisting of magnesium nitrate hexahydrate, magnesium nitrate, hydrated magnesium nitrate, magnesium chloride, hydrated magnesium chloride, magnesium chloride hexahydrate, magnesium acetate tetrahydrate, magnesium acetylacetonate dihydrate, magnesium carbonate hydroxide pentahydrate, magnesium perchlorate, magnesium perchlorate hexahydrate, magnesium sulfate, magnesium sulfate heptahydrate, magnesium sulfate monohydrate, and combinations thereof.

12. A process according to claim 9 wherein said calcium component is selected from the group consisting of calcium nitrate tetrahydrate, calcium nitrate, hydrated calcium nitrate, calcium chloride, hydrated calcium chloride, calcium chloride dihydrate, calcium chloride hexahydrate, calcium chloride hydrate, calcium acetate hydrate, calcium acetate monohydrate, calcium acetylacetonate hydrate, calcium perchlorate tetrahydrate, calcium sulfate, calcium sulfate dihydrate, calcium sulfate hemihydrate, and combinations thereof.

13. A process according to claim 9 wherein said barium component is selected from the group consisting of barium nitrate, hydrated barium nitrate, barium chloride, hydrated barium chloride, barium chloride dihydrate, barium acetate, barium acetylacetonate hydrate, barium carbonate, barium perchlorate, barium perchlorate trihydrate, barium sulfate, and combinations thereof.

14. A process according to claim 9 wherein said beryllium component is selected from the group consisting of beryllium nitrate trihydrate, hydrated beryllium nitrate, beryllium chloride, hydrated beryllium sulfate, beryllium sulfate tetrahydrate, and combinations thereof.

15. A process according to claim 9 wherein said cobalt component is selected from the group consisting of cobalt nitrate hexahydrate, hydrated cobalt nitrate, cobalt chloride, hydrated cobalt chloride, cobalt chloride hexahydrate, cobalt chloride hydrate, cobalt acetate tetrahydrate, cobalt acetylacetonate, cobalt acetylacetonate hydrate, cobalt carbonate hydrate, cobalt perchlorate hexahydrate, hydrated cobalt sulfate, cobalt sulfate hydrate, and combinations thereof.

16. A process according to claim 9 wherein said iron component is selected from the group consisting of iron nitrate nonahydrate, hydrated iron nitrate, iron chloride, hydrated iron chloride, iron chloride tetrahydrate, iron chloride hexahydrate, iron acetate, iron acetylacetonate, iron perchlorate hexahydrate, hydrated iron sulfate, iron sulfate heptahydrate, and combinations thereof.

17. A process according to claim 9 wherein said manganese component is selected from the group consisting of manganese nitrate hexahydrate, hydrated manganese nitrate, manganese nitrate hydrate, manganese chloride, hydrated manganese chloride, manganese chloride tetrahydrate, manganese acetate dihydrate, manganese acetate tetrahydrate, manganese acetylacetonate, manganese carbonate, manganese perchlorate hexahydrate, hydrated manganese sulfate, manganese sulfate monohydrate, and combinations thereof.

18. A process according to claim 9 wherein said strontium component is selected from the group consisting of strontium nitrate, hydrated strontium nitrate, strontium chloride, hydrated strontium chloride, strontium chloride hexahydrate, strontium acetate, strontium acetylacetonate, strontium carbonate, strontium perchlorate hydrate, hydrated strontium sulfate, strontium sulfate, and combinations thereof.

19. A process according to claim 9 wherein said lithium component is selected from the group consisting of lithium nitrate, hydrated lithium nitrate, lithium chloride, hydrated lithium chloride, lithium chloride hydrate, lithium acetate dihydrate, lithium acetylacetonate, lithium perchlorate, lithium perchlorate trihydrate, lithium sulfate, lithium sulfate monohydrate, and combinations thereof.

20. A process according to claim 9 wherein said potassium component is selected from the group consisting of potassium nitrate, hydrated potassium nitrate, potassium chloride, hydrated potassium chloride, potassium acetylacetonate hemihydrate, potassium carbonate sesquihydrate, potassium perchlorate, potassium sulfate, and combinations thereof.

21. A process according to claim 10 wherein said zinc component is zinc nitrate hexahydrate.

22. A process according to claim 11 wherein said magnesium component is magnesium nitrate hexahydrate.

23. A process according to claim 12 wherein said calcium component is calcium nitrate tetrahydrate.

24. A process according to claim 9 wherein said barium component is barium nitrate; said beryllium component is beryllium nitrate trihydrate; said cobalt component is cobalt nitrate hexahydrate; said iron component is iron nitrate nonahydrate; said manganese component is manganese nitrate hexahydrate; said strontium component is strontium nitrate; said lithium component is lithium nitrate; and said potassium component is potassium nitrate.

25. A process according to claim 3 wherein said temperature of said melting condition is in the range of from about 25° C. to about 160° C.

26. A process according to claim 1 wherein said metal-incorporated alumina is subjected to drying under a drying condition before being subjected to said calcining step (b).

27. A process according to claim 26 wherein said drying condition comprises:
  a temperature in the range of from about 80° C. to about 140° C.,
  a time period in the range of from about 0.5 hour to about 60 hours, and
  a pressure in the range of from about atmospheric to about 150 psia.

28. A process according to claim 1 wherein said alumina in incorporating step (a) has been heated by subjecting said alumina to a heating condition before said alumina is incorporated with said metal component and further wherein said heating condition comprises:
  a temperature in the range of from about 80° C. to about 150° C.,
  a time period in the range of from about 1 minute to about 2 hours, and
  a pressure in the range of from about atmospheric to about 150 psia.

29. A process according to claim 1 wherein after said calcining step (b) a metal aluminate forms in, on the outside surface of, or on, but not limited to, the surface of, said alumina.

30. A process according to claim 1 wherein the amount of said metal aluminate of said metal aluminate catalyst support is in the range of from about 1 weight percent based on the total weight of said metal aluminate catalyst support to about 100 weight percent; the amount of alpha alumina of said metal aluminate catalyst support is in the range of from about 0 weight percent based on the total weight of said metal aluminate catalyst support to about 99 weight percent; and the amount of gamma alumina of said metal aluminate catalyst support is in the range of from about 0 weight percent based on the total weight of said metal aluminate catalyst support to about 60 weight percent.

31. A process according to claim 30 wherein the surface area of said metal aluminate catalyst support is in the range of from about 1 m²/g to about 200 m²/g; the pore volume of said metal aluminate catalyst support is in the range of from about 0.05 mL/g to about 2 mL/g; the average pore diameter of said metal aluminate catalyst support is in the range of from about 50 angstroms to about 1000 angstroms; and the crystalline domain size of the metal aluminate of said metal aluminate catalyst support is in the range of from about 25 angstroms to about 1750 angstroms.

32. A process according to claim 31 wherein said alpha alumina of said metal aluminate catalyst support has a crystalline domain size in the range of from about 25 angstroms to about 3000 angstroms.

33. A process according to claim 1 wherein said alumina in said incorporating step (a) is selected from the group consisting of alpha alumina, beta alumina, delta alumina, eta alumina, gamma alumina and combinations thereof.

34. A process according to claim 33 wherein said alumina in said incorporating step (a) is gamma alumina.

35. A process according to claim 34 wherein said alumina in said incorporating step (a) is in the form of tablets, pellets, extrudates, spheres, and combinations thereof.

36. A process according to claim 35 wherein said alumina in said incorporating step (a) has a surface area in the range of from about 5 m²/g to about 400 m²/g; a pore volume in the range of from about 0.05 mL/g to about 2 mL/g; an average pore diameter in the range of from about 5 angstroms to about 600 angstroms; and a particle size in the range of from about 0.5 mm to about 10 mm.

37. A process according to claim 1 wherein said catalyst component is silver.

38. A process according to claim 1 wherein said catalyst component is an alkali metal compound.

39. A process according to claim 1 wherein said catalyst component is silver and an alkali metal compound.

40. A process according to claim 1 wherein said palladium is present in a palladium compound selected from the group consisting of palladium bromide, palladium chloride, palladium iodide, palladium nitrate, palladium nitrate hydrate, tetraamine palladium nitrate, palladium oxide, palladium oxide hydrate, palladium sulfate, and combinations thereof.

41. A process according to claim 40 wherein said silver is present in a silver compound selected from the group consisting of silver nitrate, silver acetate, silver cyanide and combinations thereof.

42. A process according to claim 41 wherein said alkali metal compound is selected from the group consisting of alkali metal halides, alkali metal hydroxides, alkali metal carbonates, alkali metal bicarbonates, alkali metal nitrates, alkali metal carboxylates, and combinations thereof.

43. A process according to claim 42 wherein said palladium compound is palladium chloride.

44. A process according to claim 43 wherein hydrochloric acid has been added to said palladium chloride to form a $PdCl_4^{-2}$ complex.

45. A process according to claim 43 wherein said silver compound is silver nitrate.

46. A process according to claim 45 wherein said alkali metal compound is an alkali metal halide.

47. A process according to claim 46 wherein said alkali metal compound is an alkali metal iodide or an alkali metal fluoride.

48. A process according to claim 47 wherein the alkali metal of said alkali metal compound is selected from the group consisting of potassium, rubidium, cesium, and combinations thereof.

49. A process according to claim 48 wherein said alkali metal compound is potassium iodide or potassium fluoride.

50. A process according to claim 49 wherein said alkali metal compound is potassium fluoride.

51. A process according to claim 50 wherein said catalyst component is silver nitrate.

52. A process according to claim 50 wherein said catalyst component is potassium fluoride.

53. A process according to claim 50 wherein said catalyst component is silver nitrate and potassium fluoride.

54. A process according to claim 40 wherein said palladium compound is present in a palladium-containing solution wherein the concentration of said palladium compound in said palladium-containing solution provides a catalyst composition having an amount of said palladium in the range of from about 0.0001 weight percent palladium based on the total weight of the said catalyst composition to about 3 weight percent.

55. A process according to claim 54 wherein said palladium compound is present in said palladium-containing solution in a concentration in the range of from about 0.01 mmol/L to about 5 mol/L.

56. A process according to claim 41 wherein said silver compound is present in a silver-containing solution wherein the concentration of said silver compound in said silver-containing solution provides a catalyst composition having an amount of silver in the range of from about 0.0003 weight percent silver based on the total weight of the said catalyst composition to about 20 weight percent.

57. A process according to claim 56 wherein said silver compound is present in said silver-containing solution in a concentration in the range of from about 0.01 mmol/L to about 10 mol/L.

58. A process according to claim 42 wherein said alkali metal compound is present in an alkali metal compound-containing solution wherein the concentration of said alkali metal compound in said alkali metal compound-containing solution provides a catalyst composition having an amount of alkali metal in the range of from about 0.001 weight percent alkali metal based on the total weight of the said catalyst composition to about 10 weight percent.

59. A process according to claim 58 wherein said alkali metal compound is present in said alkali metal compound-containing solution in a concentration in the range of from about 0.01 mmol/L to about 10 mol/L.

60. A process according to claim 42 wherein said alkali metal compound is an alkali metal fluoride and further wherein said alkali metal fluoride is present in an alkali metal fluoride-containing solution wherein the concentration of said alkali metal fluoride in said alkali metal fluoride-containing solution provides a catalyst composition having an amount of alkali metal in the range of from about 0.001 weight percent alkali metal based on the total weight of the said catalyst composition to about 10 weight percent.

61. A process according to claim 60 wherein said alkali metal fluoride is present in said alkali metal fluoride-containing solution in a concentration in the range of from about 0.01 mmol/L to about 10 mol/L.

62. A process according to claim 1 wherein said palladium is concentrated in the skin of said catalyst composition and further wherein said skin has a thickness in the range of from about 1 micron to about 1000 microns.

63. A process according to claim 1 wherein said process of making a catalyst composition further comprises drying, under a composition drying condition, after said impregnating said metal aluminate catalyst support with said palladium and said catalyst component, wherein said composition drying condition comprises:
   a temperature in the range of from about 35° C. to about 160° C.,
   a time period generally in the range of from about 0.5 hour to about 6 hours, and
   a pressure in the range of from about atmospheric to about 100 pounds per square inch absolute.

64. A process according to claim 63 wherein said process of making a catalyst composition further comprises calcining, under a composition calcining condition, after said drying under a composition drying condition, wherein said composition calcining condition comprises:
   calcining either in air or in a non-oxidizing gas atmosphere,
   a temperature in the range of from about 200° C. to about 800° C.,
   a time period in the range of from about 0.5 hour to about 40 hours, and
   a pressure in the range of from about 7 pounds per square inch absolute to about 750 psia.

65. A process according to claim 1 wherein said metal aluminate catalyst support is impregnated with said palladium, dried under a composition drying condition, calcined under a composition calcining condition, impregnated with said catalyst component, dried under said composition drying condition, and calcined under said composition calcining condition.

66. A process according to claim 65 wherein said catalyst component is silver.

67. A process according to claim 65 wherein said catalyst component is an alkali metal compound.

68. A process according to claim 65 wherein said catalyst component is silver and an alkali metal compound.

69. A process according to claim 1 wherein said metal aluminate catalyst support is impregnated with said catalyst component, impregnated with said palladium, dried under a composition drying condition, and calcined under a composition calcining condition.

70. A process according to claim 69 wherein said catalyst component is silver.

71. A process according to claim 69 wherein said catalyst component is an alkali metal compound.

72. A process according to claim 69 wherein said catalyst component is silver and an alkali metal compound.

73. A process according to claim 1 wherein said catalyst composition is further contacted with an aqueous solution of at least one alkali metal hydroxide.

74. A process according to claim 1 wherein said catalyst composition is further contacted with an aqueous solution of at least one alkali metal fluoride.

75. A process according to claim 1 wherein said catalyst composition is further contacted with an aqueous solution of at least one alkali metal hydroxide and at least one alkali metal fluoride.

76. A process according to claim 75 wherein said alkali metal hydroxide is potassium hydroxide and said alkali metal fluoride is potassium fluoride.

77. A process according to claim 1 wherein said catalyst composition is additionally contacted with a wet-reducing agent.

78. A process according to claim 77 wherein said wet-reducing agent is selected from the group consisting of hydrazine, an alkali metal borohydride, an aldehyde containing 1–6 carbon atoms per molecule, a ketone containing 1–6 carbon atoms per molecule, a carboxylic acid containing 1–6 carbon atoms per molecule, a reducing sugar containing an aldehyde or alpha-hydroxyketone group, and combinations thereof.

79. A process according to claim 1 wherein said catalyst composition is additionally contacted with a non-alkali metal fluoride selected from the group consisting of HF, $NH_4F$, $NH_4HF_2$, and combinations thereof.

80. A process of making a catalyst composition comprising impregnating a metal aluminate catalyst support with palladium and a catalyst component selected from the group consisting of silver and an alkali metal compound wherein said metal aluminate catalyst support is prepared by a process comprising:
   (a) impregnating alumina with a metal component to thereby provide a metal-incorporated alumina, and
   (b) calcining said metal-incorporated alumina under a calcining condition to thereby provide said metal aluminate catalyst support wherein said calcining condition comprises a temperature in the range of from about 1100° C. to about 1350° C., a pressure in the range of from about 7 pounds per square inch absolute (psia) to about 750 psia, and a time period in the range of from about 1 hour to about 60 hours; and further wherein said metal component is present in an aqueous solution formed by dissolving said metal component in a solvent selected from the group consisting of water, alcohol, esters, ethers, ketones, and combinations thereof; and said metal component is selected from the group consisting of a zinc component, a magnesium component, a calcium component, a barium component, a beryllium component, a cobalt component, an iron component, a manganese component, a strontium component, a lithium component, a potassium component, and combinations thereof.

81. A process according to claim 80 wherein said catalyst component is silver; said zinc component is zinc nitrate hexahydrate; said magnesium component is magnesium nitrate hexahydrate; said calcium component is calcium nitrate tetrahydrate; said barium component is barium nitrate; said beryllium component is beryllium nitrate trihydrate; said cobalt component is cobalt nitrate hexahydrate; said iron component is iron nitrate nonahydrate; said manganese component is manganese nitrate hexahydrate; said strontium component is strontium nitrate; said lithium component is lithium nitrate; and said potassium component is potassium nitrate; and further wherein the amount of metal aluminate of said metal aluminate catalyst support is in the range of from about 1 weight percent based on the total weight of said metal aluminate catalyst support to about 100 weight percent; the amount of alpha alumina of said metal aluminate catalyst support is in the range of from about 0 weight percent based on the total weight of said metal aluminate catalyst support to about 99 weight percent; and the amount of gamma alumina of said metal aluminate catalyst support is in the range of from about 0 weight percent based on the total weight of said metal aluminate catalyst support to about 60 weight percent.

82. A process according to claim 80 wherein said catalyst component is an alkali metal compound; said zinc component is zinc nitrate hexahydrate; said magnesium component is magnesium nitrate hexahydrate; said calcium component is calcium nitrate tetrahydrate; said barium component is barium nitrate; said beryllium component is beryllium nitrate trihydrate; said cobalt component is cobalt nitrate hexahydrate; said iron component is iron nitrate nonahydrate; said manganese component is manganese nitrate hexahydrate; said strontium component is strontium nitrate; said lithium component is lithium nitrate; and said potassium component is potassium nitrate; and further wherein the amount of metal aluminate of said metal aluminate catalyst support is in the range of from about 1 weight percent based on the total weight of said metal aluminate catalyst support to about 100 weight percent; the amount of alpha alumina of said metal aluminate catalyst support is in the range of from about 0 weight percent based on the total weight of said metal aluminate catalyst support to about 99 weight percent; and the amount of gamma alumina of said metal aluminate catalyst support is in the range of from about 0 weight percent based on the total weight of said metal aluminate catalyst support to about 60 weight percent.

83. A process according to claim 80 wherein said catalyst component is silver and an alkali metal compound; said zinc component is zinc nitrate hexahydrate; said magnesium component is magnesium nitrate hexahydrate; said calcium component is calcium nitrate tetrahydrate; said barium component is barium nitrate; said beryllium component is beryllium nitrate trihydrate; said cobalt component is cobalt nitrate hexahydrate; said iron component is iron nitrate nonahydrate; said manganese component is manganese nitrate hexahydrate; said strontium component is strontium nitrate; said lithium component is lithium nitrate; and said potassium component is potassium nitrate; and further wherein the amount of metal aluminate of said metal aluminate catalyst support is in the range of from about 1 weight percent based on the total weight of said metal aluminate catalyst support to about 100 weight percent; the amount of alpha alumina of said metal aluminate catalyst support is in the range of from about 0 weight percent based on the total weight of said metal aluminate catalyst support to about 99 weight percent; and the amount of gamma alumina of said metal aluminate catalyst support is in the range of from about 0 weight percent based on the total weight of said metal aluminate catalyst support to about 60 weight percent.

84. A composition prepared by the process of claim 1.
85. A composition prepared by the process of claim 2.
86. A composition prepared by the process of claim 3.
87. A composition prepared by the process of claim 4.
88. A composition prepared by the process of claim 5.
89. A composition prepared by the process of claim 6.
90. A composition prepared by the process of claim 7.
91. A composition prepared by the process of claim 8.
92. A composition prepared by the process of claim 9.
93. A catalyst composition comprising palladium, a metal aluminate catalyst support, and a catalyst component selected from the group consisting of silver and an alkali metal compound wherein said metal aluminate catalyst support comprises a metal aluminate and alumina and further wherein said alumina is selected from the group consisting of alpha alumina, beta alumina, delta alumina, eta alumina, gamma alumina and combinations thereof and further wherein said metal aluminate catalyst support has been calcined under a calcining condition wherein said calcining condition comprises a temperature in the range of from about 1100° C. to about 1350° C.

94. A catalyst composition according to claim 93 wherein the amount of said metal aluminate of said metal aluminate catalyst support is in the range of from about 1 weight percent based on the total weight of said metal aluminate catalyst support to about 100 weight percent.

95. A catalyst composition according to claim 94 wherein the amount of said alpha alumina of said metal aluminate catalyst support is in the range of from about 0 weight percent based on the total weight of said metal aluminate catalyst support to about 99 weight percent and further wherein the amount of said gamma alumina of said metal aluminate catalyst support is in the, range of from about 0 weight percent based on the total weight of said metal aluminate catalyst support to about 60 weight percent.

96. A catalyst composition according to claim 95 wherein said metal aluminate is selected from the group consisting of a zinc aluminate, a magnesium aluminate, a calcium aluminate, a barium aluminate, a beryllium aluminate, a cobalt aluminate, an iron aluminate, a manganese aluminate, a strontium aluminate, a lithium aluminate, a potassium aluminate and combinations thereof.

97. A catalyst composition according to claim 96 wherein said metal aluminate is selected from the group consisting of a zinc aluminate, a magnesium aluminate, a calcium aluminate, and combinations thereof.

98. A catalyst composition according to claim 97 wherein said metal aluminate is zinc aluminate.

99. A catalyst composition according to claim 98 wherein the surface area of said metal aluminate catalyst support is in the range of from about 1 m$^2$/g to about 200 m$^2$/g, the pore volume of said metal aluminate catalyst support is in the range of from about 0.05 mL/g to about 2 mL/g, the average pore diameter of said metal aluminate catalyst support is in the range of from about 50 angstroms to about 1000 angstroms, and the crystalline domain size of the metal aluminate of said metal aluminate catalyst support is in the range of from about 25 angstroms to about 1750 angstroms.

100. A catalyst composition according to claim 99 wherein said alpha alumina of said metal aluminate catalyst support has a crystalline domain size in the range of from about 25 angstroms to about 3000 angstroms.

101. A catalyst composition according to claim 93 wherein said catalyst composition has an amount of said palladium in the range of from about 0.0001 weight percent palladium based on the total weight of the said catalyst composition to about 3 weight percent.

102. A catalyst composition according to claim 93 wherein said catalyst component is silver and further wherein said catalyst composition has an amount of said silver in the range of from about 0.0003 weight percent silver based on the total weight of the said catalyst composition to about 20 weight percent.

103. A catalyst composition according to claim 93 wherein said catalyst component is an alkali metal compound and further wherein said catalyst composition has an amount of alkali metal in the range of from about 0.001 weight percent alkali metal based on the total weight of the said catalyst composition to about 10 weight percent.

104. A catalyst composition according to claim 93 wherein said catalyst component is silver and an alkali metal compound and further wherein said catalyst composition has an amount of silver in the range of from about 0.0003 weight percent silver based on the total weight of the said catalyst composition to about 20 weight percent and an amount of alkali metal in the range of from about 0.001 weight percent alkali metal based on the total weight of the said catalyst composition to about 10 weight percent.

105. A catalyst composition according to claim 93 wherein said alkali metal compound is selected from the group consisting of alkali metal halides, alkali metal hydroxides, alkali metal carbonates, alkali metal bicarbonates, alkali metal nitrates, alkali metal carboxylates, and combinations thereof.

106. A catalyst composition according to claim 105 wherein said alkali metal compound is an alkali metal iodide or an alkali metal fluoride.

107. A catalyst composition according to claim 106 wherein said alkali metal compound is potassium iodide or potassium fluoride.

108. A catalyst composition according to claim 107 wherein said alkali metal compound is potassium fluoride.

* * * * *